United States Patent
Barber

(10) Patent No.: US 11,559,549 B2
(45) Date of Patent: Jan. 24, 2023

(54) PD1-SPECIFIC CHIMERIC ANTIGEN RECEPTOR AS AN IMMUNOTHERAPY

(71) Applicant: LONGWOOD UNIVERSITY, Farmville, VA (US)

(72) Inventor: Amorette Barber, Farmville, VA (US)

(73) Assignee: LONGWOOD UNIVERSITY, Farmville, VA (US)

(*) Notice: Subject to any disclaimer, the term of this patent is extended or adjusted under 35 U.S.C. 154(b) by 156 days.

(21) Appl. No.: 16/650,884

(22) PCT Filed: Sep. 26, 2018

(86) PCT No.: PCT/US2018/052799
§ 371 (c)(1),
(2) Date: Mar. 26, 2020

(87) PCT Pub. No.: WO2019/067504
PCT Pub. Date: Apr. 4, 2019

(65) Prior Publication Data
US 2020/0281974 A1    Sep. 10, 2020

Related U.S. Application Data

(60) Provisional application No. 62/563,336, filed on Sep. 26, 2017.

(51) Int. Cl.
*A61K 35/17*    (2015.01)
*A61P 35/00*    (2006.01)
(Continued)

(52) U.S. Cl.
CPC .............. *A61K 35/17* (2013.01); *A61P 35/00* (2018.01); *C07K 14/7051* (2013.01);
(Continued)

(58) Field of Classification Search
CPC ................... A61K 35/17; A61K 45/06; A61K 2039/5156; A61K 2039/585; A61P 35/00;
(Continued)

(56) References Cited

U.S. PATENT DOCUMENTS

2016/0068601 A1    3/2016    Brogdon
2017/0136063 A1    5/2017    Perez et al.
(Continued)

FOREIGN PATENT DOCUMENTS

CN    106399255 A    *    2/2017    ....... C07K 14/70521
CN    108384795 A        8/2018
(Continued)

OTHER PUBLICATIONS

Chong, E., et al (2017) PD-1 blockade modulates chimeric antigen receptor (CAR)-modified T cells: refueling the CAR Blood 129(8); 1039-1041. (Year: 2017).*
(Continued)

*Primary Examiner* — Joanne Hama
*Assistant Examiner* — Audrey L Buttice
(74) *Attorney, Agent, or Firm* — Mintz, Levin, Cohn, Ferris, Glovsky and Popeo, P.C.

(57) ABSTRACT

Provided herein are methods and compositions useful for treating PDL1 and/or PDL2 positive cancers through adoptive cell transfer of T cells genetically engineered to express a PD1-specific chimeric antigen receptor. Co-stimulatory domains such as Dap 10 may be included to enhance efficacy.

9 Claims, 6 Drawing Sheets
Specification includes a Sequence Listing.

(51) Int. Cl.
C07K 14/725 (2006.01)
C07K 14/705 (2006.01)
C12N 15/63 (2006.01)
A61K 45/06 (2006.01)

(52) U.S. Cl.
CPC ........ *C07K 14/70532* (2013.01); *C12N 15/63* (2013.01); *A61K 45/06* (2013.01)

(58) Field of Classification Search
CPC .......... C07K 14/7051; C07K 14/70532; C07K 14/705; C07K 14/70503; C07K 14/70521; C07K 2319/00; C07K 2319/03; C07K 2319/33; C12N 15/63; C12N 2510/00
See application file for complete search history.

(56) References Cited

U.S. PATENT DOCUMENTS

2017/0218337 A1* 8/2017 Friedman ........... C07K 14/7051
2017/0246279 A1* 8/2017 Berger ........... A61K 39/001157

FOREIGN PATENT DOCUMENTS

| WO | 2016/138846 A1 | 9/2016 |
| WO | 2018/170021 A1 | 9/2018 |
| WO | 2019/067504 A1 | 4/2019 |

OTHER PUBLICATIONS

Dai, H., et al (2016) Chimeric Antigen Receptors Modified T-Cells for Cancer Therapy JNCI J Natl Cancer Inst 108(7); 1-14. (Year: 2016).*
Jin, C., et al (2016) Prospects to improve chimeric antigen receptor T-cell therapy for solid tumors Immunotherapy 8(12); 1355-1361. (Year: 2016).*
Morgan, R.A. (2016) Commentary on "A chimeric switch-receptor targeting PD1 augments the efficacy of second-generation CAR T cells in advanced solid tumors" Transitional Cancer Research 5(4): S636-S639 (Year: 2016).*
Suarez, E., et al (2016) Chimeric antigen receptor T cells secreting anti-PD-L1 antibodies more effectively regress renal cell carcinoma in a humanized mouse model Oncotarget 7(33); 34341-34355. (Year: 2016).*
Ramos, C.A., et al (2016) CAR-T Cell Therapy for Lymphoma Annu. Rev. Med. 67; 165-183 (Year: 2016).*
Yim, D., et al (2001) Molecular cloning and characterization of pig immunoreceptor DAP10 and NKG2D Immunogenetics 53; 243-249 (Year: 2001).*
International Preliminary Report on Patentability dated Apr. 9, 2020 in International Patent Application No. PCT/US2018/052799, filed on Sep. 26, 2018, 7 pages.
International Search Report and Written Opinion dated Nov. 20, 2018 in International Patent Application No. PCT/US2018/052799, filed on Sep. 26, 2018, 13 pages.
Ahmadzadeh et al., "Tumor Antigen-specific CD8 T Cells Infiltrating the Tumor Express High Levels of PD-1 and Are Functionally Impaired", Blood, Aug. 20, 2009, 114(8):1537-1544.
Ankri et al., "Human T Cells Engineered to Express a Programmed Death 1/28 Costimulatory Retargeting Molecule Display Enhanced Antitumor Activity", The Journal of Immunology, 2013, 191:4121-4129.
Ansell Stephen M., "Where Do Programmed Death-1 Inhibitors Fit in the Management of Malignant Lymphoma?", Clinical Review, Feb. 2016, 12(2):101-106.
Barber et al., "Chimeric NKG2D T Cells Require Both T Cell- and Host-Derived Cytokine Secretion and Perforin Expression to Increase Tumor Antigen Presentation and Systemic Immunity", The Journal of Immunology, Aug. 15, 2009, 183(4):2365-2372.
Barber et al., "Immunotherapy with Chimeric NKG2D Receptors Leads to Long-Term Tumor-Free Survival and Development of Host Antitumor Immunity in Murine Ovarian Cancer", The Journal of Immunology, 2008, 180:72-78.
Barber et al., "NKG2D Receptor Regulates Human Effector T-Cell Cytokine Production", Blood, Jun. 16, 2011, 117(24): 6571-6581.
Bardhan et al., "The PD1: PD-L1/2 Pathway from Discovery to Clinical Implementation", Frontiers in Immunology, Dec. 2016, 7(550):17 pages.
Benitez et al., "Expression, Signaling Proficiency, and Stimulatory Function of the NKG2D Lymphocyte Receptor in Human Cancer Cells", Proceedings of the National Academy of Sciences, Mar. 8, 2011, 108(10):4081-4086.
Blank et al., "Contribution of the PD-L1/PD-1 Pathway to T-Cell Exhaustion: An Update on Implications for Chronic Infections and Tumor Evasion", Cancer Immunology, Immunotherapy, 2007, 56:739-745.
Bonifant et al., "Toxicity and Management in CAR T-Cell Therapy", Molecular Therapy—Oncolytics, 2016, 3(16011):7 pages.
Cheadle et al., "Differential Role of Th1 and Th2 Cytokines in Autotoxicity Driven by CD19-Specific Second-Generation Chimeric Antigen Receptor T Cells in a Mouse Model", The Journal of Immunology, 2014, 192:3654-3665.
Chemnitz et al., "SHP-1 and SHP-2 Associate with Immunoreceptor Tyrosine-Based Switch Motif of Programmed Death 1 upon Primary Human T Cell Stimulation, but Only Receptor Ligation Prevents T Cell Activation", Journal of Immunology, 2004, 173:945-954.
Chmielewski et al., "Antigen-Specific T-Cell Activation Independently of the MHC: Chimeric Antigen Receptor-Redirected T Cells", Frontiers in Immunology, Nov. 11, 2013, 4(371):7 pages.
Colombetti et al., "Prolonged TCR/CD28 Engagement Drives IL-2-lndependent T Cell Clonal Expansion through Signaling Mediated by the Mammalian Target of Rapamycin", The Journal of Immunology, 2006, 176:2730-2738.
Davila et al., "Efficacy and Toxicity Management of 19-28z CAR T Cell Therapy in B Cell Acute Lymphoblastic Leukemia", Science Translational Medicine, Feb. 19, 2014, 6:224ra25:11 pages.
Holzinger et al., "The Growing World of CAR T Cell Trials: A Systematic Review", Cancer Immunology, Immunotherapy, 2016, 65:18 pages.
Hombach et al., "Of Chimeric Antigen Receptors and Antibodies: OX40 and 41BB Costimulation Sharpen up T Cell-Based Immunotherapy of Cancer", Immunotherapy, 2013, 5(7):677-681.
Hombach et al., "OX40 Costimulation by a Chimeric Antigen Receptor Abrogates CD28 and IL-2 Induced IL-10 Secretion by Redirected CD4(+) T Cells", Oncoimmunology, Jul. 2012, 1(4):458-466.
Hombach et al., "The Weal and Woe of Costimulation in the Adoptive Therapy of Cancer with Chimeric Antigen Receptor (CAR)-Redirected T Cells", Current Molecular Medicine, Aug. 2013, 13(7):1079-1088.
Ito et al., "Analysis of the Role of Negative T Cell Costimulatory Pathways in CD4 and CD8 T Cell-Mediated Alloimmune Responses In Vivo", The Journal of Immunology, 2005, 174:6648-6656.
Johnson et al., "Driving Gene-Engineered T Cell Immunotherapy of Cancer", Cell Research, 2017, 27:38-58.
Kamphorst et al., "Manipulating the PD-1 Pathway to Improve Immunity", Current Opinion in Immunology, Jun. 2013, 25(3):381-388.
Kawalekar et al., "Distinct Signaling of Coreceptors Regulates Specific Metabolism Pathways and Impacts Memory Development in CAR T Cells", Immunity, 2016, 44:380-390.
Kim et al., "Signal Integration by Akt Regulates CD8 T Cell Effector and Memory Differentiation", The Journal of Immunology, 2012, 88:4305-4314.
Kobold et al., "Impact of a New Fusion Receptor on PD-1-Mediated Immunosuppression in Adoptive T Cell Therapy", JNCI: Journal of the National Cancer Institute, 2015, 107(8): djv146:10 pages.
Kowolik et al., "CD28 Costimulation Provided through a CD19-Specific Chimeric Antigen Receptor Enhances In vivo Persistence and Antitumor Efficacy of Adoptively Transferred T Cells", Cancer Research, Nov. 15, 2006, 66(22):10995-10004.
Lee et al., "Current Concepts in the Diagnosis and Management of Cytokine Release Syndrome", Blood, 2014, 124(2):188-195.

(56) References Cited

OTHER PUBLICATIONS

Lee et al., "T Cells Expressing CD19 Chimeric Antigen Receptors for Acute Lymphoblastic Leukaemia in Children and Young Adults: A Phase 1 Dose-Escalation Trial", The Lancet, Oct. 13, 2014, 12 pages.
Lim et al., "The Principles of Engineering Immune Cells to Treat Cancer", Cell, Feb. 9, 2017, 168(4):724-740.
Liu et al., "A Chimeric Switch-Receptor Targeting PD1 Augments the Efficacy of Second-Generation CAR T Cells in Advanced Solid Tumors", Cancer Research, March 15, 2016, 76(6):1578-1590.
Maasho et al., "Cutting Edge: NKG2D Is a Costimulatory Receptor for Human Naive CD8+ T Cells", Journal of Immunology, 2005, 174:4480-4484.
Markiewicz et al., "Costimulation through NKG2D Enhances Murine CD8+ CTL Function: Similarities and Differences between NKG2D and CD28 Costimulation", The Journal of Immunology, 2005, 175:2825-2833.
McQueen et al., "Natural killergroup 2D and CD28 receptors differentially activate mammalian/mechanistic target of rapamycin to alter murine effector CD8+ T-cell differentiation", Immunology, 2016, 147:305-320.
Morales-Kastresana et al., "Better Performance of CARs Deprived of the PD-1 Brake", Clinical Cancer Research, Oct. 2013, 19(20):5546-5548.
Pardoll Drew M., "The Blockade of Immune Checkpoints in Cancer Immunotherapy", Nature Reviews Cancer, 2012, 12:252-264.
Postow et al., "Immune Checkpoint Blockade in Cancer Therapy", Journal of Clinical Oncology, Jun. 10, 2015, 33(17):1974-1982.
Prosser et al., "Tumor PD-L1 Co-Stimulates Primary Human CD8(+) Cytotoxic T Cells Modified to Express a PD1:CD28 Chimeric Receptor", Molecular Immunology, 2012, 51:263-272.
Rajasekaran et al., "Functional Dichotomy between NKG2D and CD28-Mediated Co-Stimulation in Human CD8+ T Cells", PLOS One, Sep. 2010, 5(9): e12635:10 pages.
Redeker et al., "Improving Adoptive T Cell Therapy: The Particular Role of T Cell Costimulation, Cytokines, and Post-Transfer Vaccination", Frontiers in Immunology, Sep. 2016, 7(345):17 pages.
Sadelain et al., "The Basic Principles of Chimeric Antigen Receptor (CAR) Design", Cancer Discovery, Apr. 2013, 3(4):388-398.
Savoldo et al., "CD28 Costimulation Improves Expansion and Persistence of Chimeric Antigen Receptor-Modified T Cells in Lymphoma Patients", The Journal of Clinical Investigation, May 2011, 12(5):1822-1826.
Speiser et al., "Regulatory Circuits of T Cell Function in Cancer", Nature Reviews Immunology vol. 2016, 16:13 pages.
Upshaw et al., "NKG2D-Mediated Activation of Cytotoxic Lymphocytes: Unique Signaling Pathways and Distinct Functional Outcomes", Seminars in Immunology, 2006, 18:167-175.
Wherry E. John, "T Cell Exhaustion", Nature Immunology, Jun. 2011, 12(6):492-499.
Whitman et al., "NKG2D Receptor Activation of NF-κB Enhances Inflammatory Cytokine Production in Murine Effector CD8(+) T Cells", Molecular Immunology, 2015, 63:268-278.
Xia et al., "Signaling Pathway and Dysregulation of PD1 and its Ligands in Lymphoid Malignancies", Biochimica et Biophysica Acta, Jan. 2016, 1865(1):58-71.
Yang et al., "mTOR and Metabolic Pathways in T Cell Quiescence and Functional Activation", Seminars in Immunology, 2012, 24:421-428.
Yong et al., "CAR T-Cell Therapy of Solid Tumors", Immunology and Cell Biology, 2017, 95;356-363.
Zhang et al., "Chimeric NKG2D—Modified T Cells Inhibit Systemic T-Cell Lymphoma Growth in a Manner Involving Multiple Cytokines and Cytotoxic Pathways", Cancer Research, Nov. 15, 2007, 67(22):10029-11036.
Deal et al. (Jul. 1, 2017) "Abstract 4983: T Cells Expressing Chimeric PD1 Receptors that Contain a Dap10 Costimulatory Domain are a Potential Treatment for Multiple Types of Cancer", Cancer Research, 77 (13_Supplement): 4983 (2 pages).

* cited by examiner

PD1-SPECIFIC CHIMERIC ANTIGEN RECEPTOR AS AN IMMUNOTHERAPY

CROSS REFERENCE TO RELATED APPLICATIONS

This application is a national stage filing under USC 371 of international application PCT/US2018/052799, filed Sep. 26, 2018, which claims the benefit of U.S. Provisional Application No. 62/563,336, filed Sep. 26, 2017, which are incorporated hereby by reference in their entirety for all purposes.

REFERENCE TO A SEQUENCE LISTING, A TABLE OR A COMPUTER PROGRAM LISTING APPENDIX SUBMITTED AS AN ASCII TEXT FILE

The Sequence Listing written in file 2020-03-26_14860001US_Seq.txt, created on Mar. 26, 2020, 8415 bytes, machine format IBM-PC, MS-Windows operating system, is hereby incorporated herein by reference in its entirety and for all purposes.

FIELD OF THE INVENTION

The disclosure generally relates to chimeric antigen receptors that target PD1 ligands, and genetically engineered T cells expressing the same, for the treatment of cancer. In particular, the chimeric antigen receptor may include a co-stimulatory domain, such as Dap10, to enhance efficacy of the treatment.

BACKGROUND OF THE INVENTION

Engineering T cells with chimeric antigen receptors (CARs) is one approach to increase T-cell anti-tumor efficacy. CARs are used to redirect T-cell specificity and allow MHC-independent recognition of tumor-associated antigens, so enhancing tumor targeting. Advantages to using CAR-modified T cells for cancer therapy include the ability to recognize a broad range of tumor types, overcome the mechanisms that tumors use to escape immune detection, and enhance T-cell function. However, the up-regulation of inhibitory receptor expression on T cells and expression of inhibitory ligands in the tumor microenvironment limit CAR T-cell responses and efficacy.

In cancer patients, negative regulation of immune responses often occurs after sustained activation of T cells. One such inhibitory receptor that plays an important role in inhibiting anti-tumor T-cell responses is the programmed death receptor 1 (PD1, CD279), which is up-regulated shortly after T-cell activation and inhibits multiple T-cell functions downstream of T-cell receptor and CD28 signaling including proliferation, cytokine production and cytotoxicity. The PD1 receptor binds to two different ligands, programmed death ligand 1 (PDL1, B7-H1, CD274) and programmed death ligand 2 (PDL2, B7-DC, CD273), both of which are overexpressed on many types of solid tumors and haematological malignancies, including lymphoma. Effective therapies targeting the PD1 ligands are needed.

SUMMARY OF THE INVENTION

The present disclosure provides CARs that target PD1 ligands and are suitable for adoptive T cell therapy.

One aspect of the disclosure provides a CAR polypeptide comprising an extracellular binding domain specific for at least one of programmed death ligand 1 (PDL1) and programmed death ligand 2 (PDL2); a transmembrane domain; and a cytoplasmic signaling domain. In some embodiments, the extracellular domain is a programmed death receptor 1 (PD1) extracellular domain. In some embodiments, the cytoplasmic signaling domain is a CD3ζ cytoplasmic domain. In some embodiments, the CAR polypeptide further comprises a DNAX-activating protein 10 (Dap10) co-stimulatory domain. In some embodiments, the polypeptide comprises a sequence at least 90% identical to SEQ ID NO: 3.

Another aspect of the disclosure provides T lymphocytes genetically modified to express a CAR according to the disclosure.

Another aspect of the disclosure provides a composition for adoptive cell transfer comprising T lymphocytes of the disclosure and a pharmaceutically acceptable carrier. In some embodiments, the composition further comprises one or more chemotherapeutic or radiotherapeutic agents.

Another aspect of the disclosure provides a method of treating cancer in a subject in need thereof, wherein cells of said cancer express at least one of PDL1 and PDL2, comprising administering to the subject a therapeutically effective amount of a composition for adoptive cell transfer according to the disclosure. In some embodiments, the cancer is selected from the group consisting of lymphoma, melanoma, myeloma, pancreatic cancer, breast cancer, and ovarian cancer.

DETAILED DESCRIPTION OF THE INVENTION

Figure 1A:
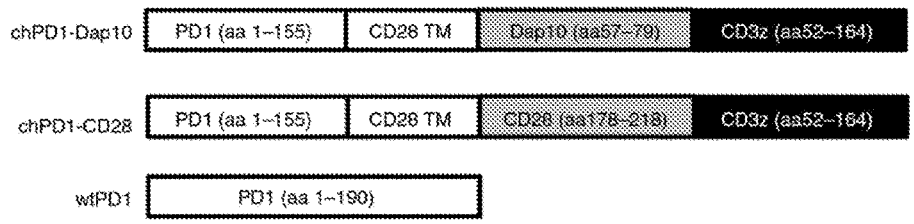
FIG. 1A-F. Chimeric programmed death 1 (chPD1) T cells lyse programmed death ligand (PDL)-expressing RMA cells in a PD1-dependent manner. (a) Representative vector map of the chPD1-Dap10, chPD1-CD28, and wild-type (wt) PD1 receptors. (b) Effector murine non-transduced, wtPD1, or chPD1 (black) T cells were stained with anti-PD1 or isotype control antibodies or (c) murine chPD1 T cells were stained with anti-PDL1 or anti-PDL2 or isotype control antibodies and were analysed using flow cytometry. (d) RMA cells were stained with anti-PDL1 or -PDL2 or isotype control antibodies and were analysed using flow cytometry. (e) Non-transduced (squares), wtPD1 (triangles) or chPD1 (circles) T cells were used as effector cells with RMA cells at the indicated effector to target (E:T) ratios (1:1, 5:1, 25:1) and cell lysis was measured using a lactate dehydrogenase assay. chPD1 T cells had significantly higher specific lysis at all E:T ratios compared with non-transduced or wtPD1 T cells ($*P<0\bullet0001$). (f) To show PD1 receptor dependence, wtPD1 or chPD1 T cells were incubated with anti-PD1 antibodies (open symbols), or with control IgG antibodies (closed symbols) before incubation with tumor cells. Blocking the PD1 receptor significantly reduced the cytotoxicity of chPD1 T cells against tumor cells at all ratios compared with control ($*P<0\bullet001$). Data are presented as mean+SD and are representative of at least three experiments.

Immunotherapy that harnesses the host immune system to fight cancer provides an important option for the treatment of cancer. T cells protect individuals from disease by targeting and eliminating diseased cells. Tumor-specific T cells can be isolated, followed by activation and expansion outside the body, and then re-infused back into the patient to mediate cancer regression, a process termed adoptive T cell therapy.

Provided herein are CARs that target PD1 ligands, i.e. that target at least one of PDL1 or PDL2. The chimeric PD1 receptor (chPD1) polypeptide may comprise an extracellular binding domain specific for at least one of PDL1 and PDL2; a transmembrane domain; and a cytoplasmic signaling domain.

As used herein, the terms "peptide," "polypeptide," and "protein" are used interchangeably, and refer to a compound having amino acid residues covalently linked by peptide bonds. A protein or peptide must contain at least two amino acids, and no limitation is placed on the maximum number of amino acids that can include a protein's or peptide's sequence. Polypeptides include any peptide or protein having two or more amino acids joined to each other by peptide bonds. As used herein, the term refers to both short chains, which also commonly are referred to in the art as peptides, oligopeptides, and oligomers, for example, and to longer chains, which generally are referred to in the art as proteins, of which there are many types.

"Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The extracellular binding domain specific for (i.e. that targets, recognizes, or binds) at least one of PDL1 and PDL2 may be the extracellular domain of the PD1 (CD279) receptor. The PD1 receptor is a protein found on the surface of cells, such as T lymphocytes, that has a role in regulating the immune system's response to an individual's own cells. In humans, the PD1 protein is encoded by the PDCD1 gene. A representative amino acid sequence for PD1 is provided in SEQ ID NO: 1. In some embodiments, the domain comprises or consists of amino acids 1-155 of PD1.

The transmembrane domain includes a hydrophobic polypeptide that spans the cellular membrane. In particular, the transmembrane domain spans from one side of a cell membrane (extracellular) through to the other side of the cell membrane (intracellular or cytoplasmic). The transmembrane domain may be in the form of an alpha helix or a beta barrel, or combinations thereof. The transmembrane domain may include a polytopic protein, which has many transmembrane segments, each alpha-helical, beta sheets, or combinations thereof. In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex.

For example, a transmembrane domain includes a transmembrane domain of a T-cell receptor α or β chain, a CD3 zeta chain, CD28, CD3ε, CD45, CD4, CD5, CD8, CD9, CD16, CD22, CD33, CD37, CD64, CD80, CD86, CD134, CD137, ICOS, CD154, functional derivatives thereof, and combinations thereof.

An artificially designed transmembrane domain is a polypeptide mainly comprising hydrophobic residues such as leucine and valine. In one embodiment, a triplet of phenylalanine, tryptophan and valine is found at each end of the synthetic transmembrane domain.

A cytoplasmic signaling domain of a CAR may be responsible for intracellular signaling following the binding of extracellular ligand binding domain to the target resulting in the activation or inhibition of the immune cell and immune response. In other words, the signal transducing domain may be responsible for the activation or inactivation of at least one of the normal effector functions of the immune cell in which the CAR is expressed. Thus, the term "cytoplasmic signaling domain" refers to the portion of a protein which transduces the effector signal function signal and directs the cell to perform a specialized function. Examples of signal transducing domain for use in CARs of the present disclosure can be the cytoplasmic sequences of the T cell receptor and co-receptors that act in concert to initiate signal transduction following antigen receptor engagement, as well as any derivative or variant of these sequences and any synthetic sequence that has the same functional capability. Cytoplasmic signaling sequences can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM can include as non limiting examples those derived from TCRzeta, FcRgamma, FcRbeta, FcRepsilon, CD3gamma, CD3delta, CD3epsilon, CD5, CD22, CD79a, CD79b and CD66d. In some embodiments, the signaling transducing domain of the CAR comprises a CD3zeta signaling domain. In some embodiments, the signaling transducing domain comprises or consists of amino acids 52-164 of CD3zeta.

In some embodiments, the inhibitory domains of PD1 are replaced with the activating domains of the cytoplasmic signaling domain, thus switching the negative PD1 signal to become an activating signal for the T cells. This should reduce the immune suppressive effects of PD1 and instead induce anti-tumor immunity upon interaction with PD1 ligands.

Inclusion of co-stimulatory domains in CART cells can enhance T-cell functions, including cytokine secretion, differentiation, cytotoxicity, proliferation and survival. Co-stimulatory receptors that are compatible with CARs of the present disclosure include, but are not limited to, functional domains from Dap10, CD28, OX40, ICOS, 4-1BB (CD137), NKG2C, and NKG2D, and active fragments, functional derivatives, and combinations thereof. As shown in Example 1, CD28 and Dap10 activate many similar pathways including phosphatidylinositol-3 kinase, AKT/Protein Kinase B and mitogen-activate protein kinases. However, CD28 and Dap10 stimulation seem to have unique effects on effector T cells, including differential activation of signal transduction pathways including β-catenin, nuclear factor-κB and mammalian target of rapamycin (mTOR), leading to dissimilar cytokine secretion and T-cell differentiation. Specifically, when compared with CD28, co-stimulation through Dap10 induces CD8 T-cell memory differentiation and secretion of pro-inflammatory but not anti-inflammatory cytokines, both of which seem to be preferable characteristics for successful CAR T-cell therapy. Hence, in some embodiments, inclusion of the Dap10 co-stimulatory domain in CARs may be preferential to CD28.

Functional-conservative derivatives or variants of a polypeptide as disclosed herein may result from modifications and changes that may be made in the structure of the polypeptide (and in the DNA sequence encoding it), and still obtain a functional molecule with desirable characteristics (e.g. tumoricidal and/or immunostimulatory effects). Functional-conservative derivatives may also consist of a fragment of a polypeptide that retains its functionality.

Accordingly, functional-conservative derivatives or variants are those in which a given amino acid residue in a protein has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A functional-conservative derivative also includes a polypeptide which has at least 70%, 75%, 80%, 85%, 90%, or 95 or more amino acid identity as determined by BLAST or FASTA algorithms and which has the same or substantially similar properties or functions as the native or parent protein to which it is compared. For example, certain amino acids may be substituted for other amino acids in a protein structure without appreciable loss of tumoricidal effects. Since it is the interactive capacity and nature of a protein that defines that protein's biological functional activity, certain amino acid substitutions can be made in a protein sequence, and, of course, in its DNA encoding sequence, and nevertheless obtain a protein with like properties. It is thus contemplated that various changes may be made in the polypeptide sequences of the disclosure, or corresponding DNA sequences which encode said polypeptides, without appreciable loss of their biological activity. Said tumoricidal activity and immunostimulatory activity can be assessed by various techniques well-known in the art, such as for instance the assays referred to in the Examples.

As outlined above, conservative amino acid substitutions are generally therefore based on the relative similarity of the amino acid side-chain substituents, for example, their hydrophobicity, hydrophilicity, charge, size, and the like. Exemplary substitutions which take several of the foregoing characteristics into consideration are well known to those of skill in the art and include: arginine and lysine; glutamate and aspartate; serine and threonine; glutamine and asparagine; and valine, leucine and isoleucine.

A polynucleotide of the disclosure can be cloned into a vector. A "vector" is a composition of matter which includes an isolated polynucleotide and which can be used to deliver the isolated polynucleotide to the interior of a cell. Numerous vectors are known in the art including, but not limited to, linear polynucleotides, polynucleotides associated with ionic or amphiphilic compounds, plasmids, phagemid, cosmid, and viruses. Viruses include phages, phage derivatives. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

In one embodiment, vectors include cloning vectors, expression vectors, replication vectors, probe generation vectors, integration vectors, and sequencing vectors. In an embodiment, the vector is a viral vector. In an embodiment, the viral vector is a retroviral vector or a lentiviral vector. In an embodiment, an engineered cell is virally transduced to express the polynucleotide sequence.

Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endomiclease sites, and one or more selectable markers.

Expression of chimeric antigen receptor polynucleotide may be achieved using, for example, expression vectors including, but not limited to, at least one of a SFFV or human elongation factor 11a (EF) promoter, CAG (chicken beta-actin promoter with CMV enhancer) promoter human elongation factor 1a (EF) promoter. Examples of less-strong/lower-expressing promoters utilized may include, but is not limited to, the simian virus 40 (SV40) early promoter, cytomegalovirus (CMV) immediate-early promoter, Ubiquitin C (UBC) promoter, and the phosphoglycerate kinase 1 (PGK) promoter, or a part thereof. Inducible expression of chimeric antigen receptor may be achieved using, for example, a tetracycline responsive promoter, including, but not limited to, TRE3GV (Tet-response element, including all generations and preferably, the 3rd generation), inducible promoter (Clontech Laboratories, Mountain View, Calif.) or a part or a combination thereof.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Adoptive T cell therapy involves isolating T cells from an individual's blood and genetically engineering those T cells to express a CAR of the disclosure. The engineered T cells are then grown ex vivo and infused back into the individual. The CAR T cells can then bind the targeted antigen on cancer cells and kill them.

An embodiment of the disclosure provides an engineered cell, e.g. a T cell/lymphocyte, expressing a CAR polypeptide as described herein or polynucleotide encoding for the same, and described herein. An "engineered cell" means any cell of any organism that is modified, transformed, or manipulated by addition or modification of a gene, a DNA or RNA sequence, or protein or polypeptide. Isolated cells, host cells, and genetically engineered cells of the present disclosure include isolated immune cells, such as NK cells and T cells that contain the DNA or RNA sequences encoding a CAR or CAR complex and express the chimeric receptor on the cell surface. Isolated host cells and engineered cells may be used, for example, for enhancing an NK cell activity or a T lymphocyte activity, treatment of cancer, and treatment of infectious diseases.

Any cell capable of expressing and/or capable of integrating the chimeric antigen receptor polypeptide, as disclosed herein, into its membrane may be used. In an embodiment, the engineered cell includes immunoregulatory cells.

Immunoregulatory cells include T-cells (or T lymphocytes), such as CD4 T-cells (Helper T-cells), CD8 T-cells (Cytotoxic T-cells, CTLs), and memory T cells or memory stem cell T cells. In another embodiment, T-cells include Natural Killer T-cells (NK T-cells).

An embodiment of the disclosure provides a method of treating cancer in a subject in need thereof, wherein cells of said cancer express at least one of PDL1 and PDL2, comprising administering to the subject a therapeutically effective amount of a composition comprising T cells genetically engineered to express a CAR according to the disclosure.

Depending upon the nature of the cells, the cells may be introduced into a host organism, e.g. a mammal, in a wide variety of ways. The cells may be introduced at the site of the tumor, in specific embodiments, although in alternative embodiments the cells hone to the cancer or are modified to hone to the cancer. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest. The cells may be in a physiologically-acceptable medium.

In particular embodiments, the route of administration may be intravenous, intraarterial, intraperitoneal, or subcutaneous, for example. Multiple administrations may be by the same route or by different routes. In some embodiments, multiple doses, e.g. 2, 3, 4, 5, or more doses are given over a period of time, e.g. over 2, 3, 4, 5, 6, 7, 8, 9, 10, or more days.

One of the adverse effects following infusion of CAR T cells is the onset of immune activation, known as cytokine release syndrome (CRS). In some embodiments, a co-stimulatory domain that does not induce elevation of one or more cytokines selected from IFN-γ, GM-CSF, IL-10 and IL-6 is used. In some embodiments, a CRS therapy such as tocilizumab (an IL-6 antagonist) is administered concomitantly or sequentially with the CAR of the disclosure. In some embodiments, radiotherapy and/or chemotherapy is administered concomitantly or sequentially with the CAR of the disclosure.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness.

The term "cancer metastasis" has its general meaning in the art and refers to the spread of a tumor from one organ or part to another non-adjacent organ or part.

Any cancer or metastatic cancer expressing at least one of PDL1 and PDL2 may be targeted using the inventive therapy including, but not limited to, lymphoma, melanoma, myeloma, pancreatic cancer, breast cancer, ovarian cancer, prostate cancer, brain cancer, liver cancer, kidney cancer, lung cancer, spleen cancer, gall bladder cancer, anal cancer, testicular cancer, ovarian cancer, cervical cancer, skin cancer, bone cancer, and colon cancer.

The terms "subject" and "patient" are used interchangeably herein, and refer to an animal such as a mammal, which is afflicted with or suspected of having, at risk of, or being pre-disposed to cancer. The terms may refer to a human. The terms also include domestic animals bred for food, sport, or as pets, including horses, cows, sheep, poultry, fish, pigs, cats, dogs, and zoo animals, goats, apes (e.g. gorilla or chimpanzee), and rodents such as rats and mice. Typical subjects include persons susceptible to, suffering from or that have suffered from cancer.

The term "treating" or "treatment", as used herein, means reversing, alleviating, inhibiting the progress of, or ameliorating the disorder or condition to which such term applies, or one or more symptoms of such disorder or condition. For example, the treatment of the disclosure may slow the growth of said cancer, reduce the number of tumor cells in said cancer, reduce tumor load, or eliminate said cancer.

By a "therapeutically effective amount" is meant a sufficient amount of the molecule to treat a cancer, (for example, to limit tumor growth or to slow or block tumor metastasis) at a reasonable benefit/risk ratio applicable to any medical treatment. It will be understood, however, that the total daily usage of the molecules and compositions of the present disclosure will be decided by the attending physician within the scope of sound medical judgment. The specific therapeutically effective dose level for any particular subject will depend upon a variety of factors including the disorder being treated and the severity of the disorder; activity of the specific polypeptide employed; the specific composition employed, the age, body weight, general health, sex and diet of the subject; the time of administration, route of administration, and rate of excretion of the specific polypeptide employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved.

The T cell therapy described herein may be combined with standard-of-care treatments (e.g., radiation therapy, hormonal therapy). In some embodiments, the T lymphocytes of the disclosure may be administered sequentially or concomitantly with one or more chemotherapeutic or radiotherapeutic agents.

In one embodiment, said chemotherapeutic or radiotherapeutic agents are a therapeutic active agent used as anticancer agent. For example, said anticancer agents include but are not limited to fludarabine, gemcitabine, capecitabine, methotrexate, mercaptopurine, thioguanine, hydroxyurea, cytarabine, cyclophosphamide, ifosfamide, nitrosoureas, platinum complexes such as cisplatin, carboplatin and oxaliplatin, mitomycin, dacarbazine, procarbazine, epipodophyllotoxins such as etoposide and teniposide, camptothecins such as irinotecan and topotecan, bleomycin, doxorubicin, idarubicin, daunorubicin, dactinomycin, plicamycin, mitoxantrone, L-asparaginase, doxorubicin, epirubicin, 5-fluorouracil and 5-fluorouracil combined with leucovorin, taxanes such as docetaxel and paclitaxel, levamisole, estramustine, nitrogen mustards, nitrosoureas such as carmustine and lomustine, vinca alkaloids such as vinblastine, vincristine, vindesine and vinorelbine, imatinib mesylate, hexamethylmelamine, kinase inhibitors, phosphatase inhibitors, ATPase inhibitors, tyrphostins, protease inhibitors, inhibitors herbimycin A, genistein, erbstatin, and lavendustin A. In one embodiment, additional anticancer agents may be selected from, but are not limited to, one or a combination of the following class of agents: alkylating agents, plant alkaloids, DNA topoisomerase inhibitors, antifolates, pyrimidine analogs, purine analogs, DNA antimetabolites, taxanes, podophyllotoxins, hormonal therapies, retinoids, photosensitizers or photodynamic therapies, angiogenesis inhibitors, antimitotic agents, isoprenylation inhibitors, cell cycle inhibitors, actinomycin, bleomycin, anthracyclines, MDR inhibitors and $Ca^{2+}$ ATPase inhibitors.

Additional anticancer agents may be selected from, but are not limited to, cytokines, chemokines, growth factors, growth inhibitory factors, hormones, soluble receptors, decoy receptors, monoclonal or polyclonal antibodies, mono-specific, bi-specific or multi-specific antibodies, monobodies, polybodies.

Further therapeutic active agents may be an antiemetic agent. Suitable antiemetic agents include, but are not limited to, metoclopramide, domperidone, prochlorperazine, promethazine, chlorpromazine, trimethobenzamide, ondansetron, granisetron, hydroxyzine, acetylleucine, alizapride, azasetron, benzquinamide, bietanautine, bromopride, buclizine, clebopride, cyclizine, dimenhydrinate, diphenidol, dolasetron, meclizine, methallatal, metopimazine, nabilone, pipamazine, scopolamine, sulpiride, tetrahydrocannabinols, thiethylperazine, thioproperazine and tropisetron. In a preferred embodiment, the antiemetic agent is granisetron or ondansetron.

In still another embodiment, the other therapeutic active agent can be an opioid or non-opioid analgesic agent. Suitable opioid analgesic agents include, but are not limited to, morphine, heroin, hydromorphone, hydrocodone, oxymorphone, oxycodone, metopon, apomorphine, buprenorphine, meperidine, loperamide, ethoheptazine, betaprodine, diphenoxylate, fentanyl, sufentanil, alfentanil, remifentanil, levorphanol, dextromethorphan, phenazone, pemazocine, cyclazocine, methadone, isomethadone and propoxyphene. Suitable non-opioid analgesic agents include, but are not limited to, aspirin, celecoxib, rofecoxib, diclofenac, diflunisal, etodolac, fenoprofen, flurbiprofen, ibuprofen, ketoprofen, indomethacin, ketorolac, meclofenamate, mefenamic acid, nabumetone, naproxen, piroxicam and sulindac.

In yet another embodiment, the further therapeutic active agent can be an anxiolytic agent. Suitable anxiolytic agents include, but are not limited to, buspirone, and benzodiazepines such as diazepam, lorazepam, oxazapam, clorazepate, clonazepam, chlordiazepoxide and alprazolam.

The term "radiotherapeutic agent" as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, and/or another radiotherapy.

Another aspect of the disclosure relates to a pharmaceutical composition comprising a T lymphocyte according to the disclosure and a pharmaceutically acceptable carrier. Pharmaceutically" or "pharmaceutically acceptable" refer to molecular entities and compositions that do not produce an adverse, allergic or other untoward reaction when administered to a subject, such as a human, as appropriate. A pharmaceutically acceptable carrier or excipient refers to a non-toxic solid, semi-solid or liquid filler, diluent, encapsulating material or formulation auxiliary of any type.

The T lymphocytes of the disclosure may be contained in physiological saline, phosphate buffered saline (PBS), culture medium, or the like in order to maintain stability.

In some embodiments, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the disclosure as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the T lymphocytes in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

In addition to the compositions of the disclosure formulated for parenteral administration, such as intravenous or intramuscular injection, other pharmaceutically acceptable forms include, e.g. tablets or other solids for oral administration; liposomal formulations; time release capsules; and any other form currently used.

Any of the compositions described herein may be comprised in a kit. In a non-limiting example, one or more cells for use in cell therapy that harbors recombinantly expressed CARs according to the disclosure and/or the reagents to generate one or more cells for use in cell therapy may be comprised in a kit. The kit components are provided in suitable container means. In specific embodiments, the kits comprises recombinant engineering reagents, such as vectors, primers, enzymes (restriction enzymes, ligase, polymerases, etc.), buffers, nucleotides, etc.

Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the components in close confinement for commercial sale. Such containers may include injection or blow-molded plastic containers into which the desired vials are retained.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example 1. Adoptive Transfer of Murine T Cells Expressing a Chimeric-PD1-Dap10 Receptor as an Immunotherapy for Lymphoma Summary Adoptive transfer of T cells is a promising cancer therapy and expression of chimeric antigen receptors can enhance tumor recognition and T-cell effector functions. Provided herein is a murine chimeric PD1 receptor (chPD1) comprising the PD1 extracellular domain fused to the cytoplasmic domain of CD3ζ. Additionally, chimeric antigen receptor therapies use various co-stimulatory domains to enhance efficacy. Hence, the inclusion of a Dap10 or CD28 co-stimulatory domain in the chPD1 receptor was compared to determine which domain induced optimal anti-tumor immunity in a mouse model of lymphoma. The chPD1 T cells secreted pro-inflammatory cytokines and lysed RMA lymphoma cells. Adoptive transfer of chPD1 T cells significantly reduced established tumors and led to tumor-free survival in lymphoma-bearing mice. When comparing chPD1 receptors containing a Dap10 or CD28 domain, both receptors induced secretion of pro-inflammatory cytokines; however, chPD1-CD28 T cells also secreted anti-inflammatory cytokines whereas chPD1-Dap10 T cells did not. Additionally, chPD1-Dap10 induced a central memory T-cell phenotype compared with chPD1-CD28, which induced an effector memory phenotype. The chPD1-Dap10 T cells also had enhanced in vivo persistence and anti-tumor efficacy compared with chPD1-CD28 T cells. Therefore, adoptive transfer of chPD1 T cells represents a novel therapy for lymphoma and inclusion of the Dap10 co-stimulatory domain in chimeric antigen receptors may induce a preferential cytokine profile and T-cell differentiation phenotype for anti-tumor therapies.

Materials and Methods

Generation of wtPD1 and chPD1 Constructs

Murine cDNA clones of CD3ζ, PD1, CD28 and Dap10 were purchased from OriGene (Rockville, Md.). The chPD1-Dap10 and chPD1-CD28 receptors were created by overlapping PCR using Phusion® high fidelity DNA polymerase (New England BioLabs, Ipswich, Mass.). To create the chPD1-Dap10 receptor, the extracellular domain of the murine PD1 receptor [amino acids (aa) 1-155] was fused in frame to the transmembrane region of CD28 (aa 141-177) and the cytoplasmic domains of Dap10 (aa 57-79) and CD3ζ (aa 52-164). To create the chPD1-CD28 receptor, the extracellular domain of the murine PD1 receptor (aa 1-155) was fused in frame to the transmembrane (aa 141-177) and cytoplasmic (aa 178-218) domains of CD28 and CD3ζ (aa 52-164). To create the wild-type PD1 (wtPD1) receptor, the extracellular and transmembrane domain of the PD1 receptor (aa 1-190) was used. All constructs were cloned into the pQCXIN retroviral expression vector using Nod and EcoRI digestion of the plasmid and constructs and were subsequently ligated into the vector. Ecotropic retroviral supernatants were expressed using the EcoPack 2-293 cell line according to the manufacturer's instructions (Clontech, Mountain View, Calif.). Xfect polymer was used to co-transfect EcoPack 2-293 cells with the pEco envelope vector and the pQCXIN retroviral expression vector from the RetroX-Q vector set (Clontech). RetroX Concentrator was used to concentrate the ecotropic retroviral supernatants before transduction of primary murine T cells.

Expression of wtPD1 and chPD1 Receptors in T Cells

Male C57BL/6 (B6) and B6.SJL-Ptprc$^a$ (Ly5.1 congenic) mice were purchased from Taconic Biosciences (Hudson, N.Y.). Mice were between 8 and 12 weeks of age at the start of each experiment. All animal work was performed in accordance and with approval from Longwood University's Institutional Animal Use and Care Committee. Splenocytes from B6 or Ly5.1 congenic mice were activated with concanavalin A (1 µg/ml) for 18 hr. T cells (0•5×10$^6$ cells/ml) were transduced by centrifugation at 1000 g for 1 hr in the presence of 8 µg/ml polybrene and 25 U/ml recombinant human interleukin-2 (IL-2) and were subsequently cultured for 6 hr before retroviral supernatants were removed and replaced with fresh complete RPMI-1640 medium supplemented with 10% heat-inactivated fetal bovine serum, 100 U/ml penicillin, 100 µg/ml streptomycin, 1 mM pyruvate, 10 mM HEPES, 0•1 mM non-essential amino acids and 50 µM 2-mercaptoethanol. Two days after infection, T cells were selected in complete RPMI-1640 medium containing G418 (0•5 mg/ml) plus 25 U/ml recombinant human IL-2 for an additional 3 days. Viable cells were isolated using Histopaque-1083 (Sigma, St Louis, Mo.) and expanded for an additional 2 days without G418 before functional analysis.

RT-PCR

Total RNA was isolated from RMA cells or T cells using the SV Total RNA isolation kit according to the manufacturer's instructions (Promega, Madison, Wis.). cDNA was created using RevertAid First Strand cDNA synthesis kit using random hexamer primers (Fermentas, Waltham, Mass.). As a template for RT-PCR, 100 ng of cDNA was used to measure gene expression of PDL1, PDL2 and β-actin. Maxima SYBRGreen qPCR Master Mix (Thermo Scientific, Waltham, Mass.) and gene specific primers were used: β-actin F 5'-GTGTGATGGTGGGAATGGGTCAGA-3' (SEQ ID NO: 4), β-actin R 5'-TACGACCAGAGGCATA-CAGGGACA-3' (SEQ ID NO: 5), PDL1 F 5'-GCTC-CAAAGGACTTGTACGTG-3' (SEQ ID NO: 6), PDL1 R 5'-TGATCTGAAGGGCAGCATTTC-3' (SEQ ID NO: 7), PDL2 F 5'-CTGCCGATACTGAACCTGAGC-3' (SEQ ID NO: 8), PDL2 R 5'-GCGGTCAAAATCGCACTC-3' (SEQ ID NO: 9). Gene-specific primers for T-cell differentiation genes T-bet, BLIMP1, Eomes and BCL6 were previously described. Primers were purchased from Integrated DNA Technologies (Coralville, Iowa).

Flow Cytometry

The expression of PDL1 and PDL2 on RMA and T cells and of PD1 on T cells was tested using flow cytometry. Cells were stained with allophycocyanin-labelled anti-PDL1 (clone 10F.9G2), phycoerythrin-labelled anti-PDL2 (clone TY25), or phycoerythrin-labelled anti-PD1 (clone RMP1-30) antibodies or isotype controls. For T-cell differentiation studies, wtPD1 or chPD1 T cells ($2 \times 10^5$ cells/well) were stimulated with RMA cells ($2 \times 10^5$ cells/well) for 24 hr and were analysed for cell surface marker expression by flow cytometry. Cells were stained with phycoerythrin-conjugated anti-CD127 (clone A7R34) or anti-KLRG1 (clone 2F1/KLRG1) and allophycocyanin-conjugated anti-CD62L (clone MEL-14) or isotype controls. To analyse T-cell surface expression, RMA cells were labelled with CFSE before incubation and CFSE$^+$ cells were gated out. All antibodies were purchased from BioLegend (San Diego, Calif.). Cell fluorescence was measured using an Accuri C6 flow cytometer.

Cytokine Production and Cytotoxicity by chPD1 T Cells

The chPD1, wtPD1 and non-transduced T cells ($10^5$) were cultured with RMA cells ($10^5$) or medium in a round-bottom 96-well plate. After 24 hr, cell-free supernatants were tested for the presence of interferon-γ (IFN-γ), tumor necrosis factor-α (TNF-α), granulocyte-macrophage colony-stimulating factor (GM-CSF), IL-2 and IL-10 by ELISA according to the manufacturer's instructions (BioLegend). Cytokine and chemokine secretion was also measured in cell-free supernatants using mouse T helper cytokine and mouse pro-inflammatory chemokine LEGENDPlex assays (BioLegend) according to the manufacturer's instructions.

To determine lysis of tumor cells, chPD1, wtPD1 and non-transduced T cells ($10^5$) were cultured with RMA at various effector to target ratios (E:T 25:1, 5:1, and 1:1). Specific lysis was measured after 5 hr using a lactate dehydrogenase cytotoxicity assay kit (Pierce, Waltham, Mass.) according to the manufacturer's instructions. To block PD1 receptors, T cells were pre-incubated at 37° for 2 hr with anti-PD1 monoclonal antibodies (clone RMP1-14, 20 μg/ml, Low Endotoxin, Azide-Free LEAF purified, BioLegend) or isotype control monoclonal antibodies before addition of target cells.

Treatment of Mice with Genetically Modified T Cells

RMA and RMA-GFP cells were grown in complete RPMI-1640. RMA-GFP cells ($2 \times 10^6$) were injected intravenously into B6 mice. For tumor burden experiments, mice were administered one dose of wtPD1 or chPD1-modified T cells ($5 \times 10^6$) intravenously 2 days or 5 days after tumor injection, or two doses of T cells 5 and 8 days after tumor injection. For determination of tumor burden, spleens and lymph nodes (axillary, brachial and inguinal) were collected 13 days after tumor injection. The lymphoid tissues were mechanically teased and red blood cells were lysed with ACK lysis buffer (0•15 mol/l NH$_4$Cl, 1 mmol/l KHCO$_3$, 0•1 mmol/l). Cells were counted and the percentage of GFP$^+$ cells was determined via flow cytometry. The total number of tumor cells was determined by multiplying the percentage of GFP$^+$ cells by the total number of cells. For survival studies, mice were treated with wtPD1 or chPD1 T cells ($5 \times 10^6$) on day 5 and 8 after tumor cell injection. The health of the mice was monitored closely and mice were killed when signs of stress (labored breathing, dragging legs, hunched back, or ruffled fur) were observed. For analysis of T-cell survival, RMA-bearing mice were treated 5 days after tumor cell injection with congenic Ly5.1$^+$ chPD1-Dap10 or chPD1-CD28 T cells ($5 \times 10^6$) intravenously and mice were killed 1, 3, 7, 10, 14 or 18 days after T-cell injection. Spleen and lymph node cells were incubated with FcR block and mouse γ-globulin (Jackson ImmunoResearch, West Grove, Pa.) to prevent non-specific binding, and stained with phycoerythrin-conjugated anti-CD3 and allophycocyanin-conjugated anti-CD45.1 (clone A20) and analysed by flow cytometry.

Statistical Analysis

Statistical analysis was conducted using an unpaired, two-tailed Student's t-test or analysis of variance with a post-hoc Tukey test when comparing multiple groups. The data were determined to be normally distributed using the Shapiro-Wilk test. The program R was used for statistical analysis of the data. All experiments were run in triplicate on at least two independent sets of T cells and P values<0•05 were considered significant. For survival studies, Kaplan-Meier survival curves were plotted and analysed using the Log rank test and PRISM software (GRAPHPAD Software, San Diego, Calif.).

Figure 1B:
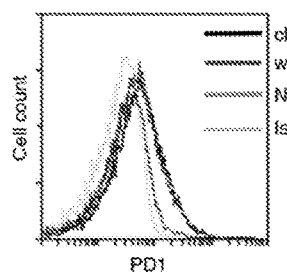

Results chPD1 T Cells Secrete Pro-Inflammatory Cytokines and Lyse PDL-Expressing RMA Cells in a PD1-Dependent Manner To target PD1 ligands expressed on tumor cells, a chPD1 receptor was created by fusing the extracellular region of the PD1 receptor with the intracellular regions of the Dap10 co-stimulatory receptor and CD3ζ (FIG. 1a). A wtPD1 receptor consisting of the extracellular and transmembrane domains of the PD1 receptor was also created as a control. The chPD1 and wtPD1 receptors were successfully expressed in activated murine T cells as shown by an increased cell surface expression of the PD1 receptor compared with non-transduced, activated T cells (FIG. 1b). Both wtPD1 and chPD1 T cells consisted of a mix of activated CD4$^+$ (~10%) and CD8$^+$ (~90%) T cells.

Figure 1C:
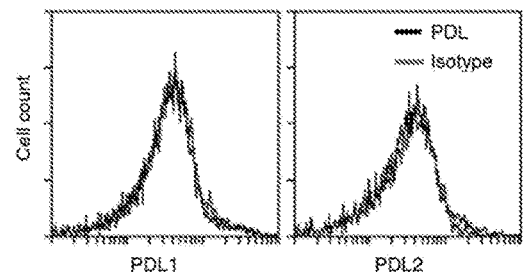

Sometimes activated T cells express PDL1, which could potentially cause chPD1 T cells to kill each other.[9] Therefore, the expression of PDL1 and PDL2 was assessed on chPD1 T cells. The number of chPD1 T cells obtained was similar to the number of wtPD1 T cells for all T-cell batches tested. In addition, significant PDL1 or PDL2 expression on chPD1 and wtPD1 T cells was not observed (FIG. 1c). Finally, a significant level of cell death was not observed when wtPD1 or chPD1 T cells were cultured in media only. These data suggest that chPD1 T cells do not express significant levels of PDL.

Figure 1D:
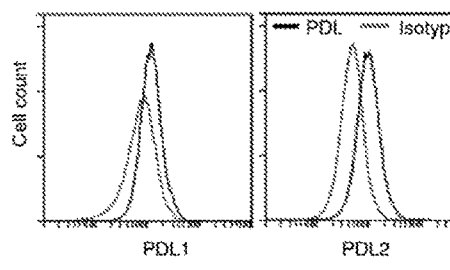
Figure 1E:
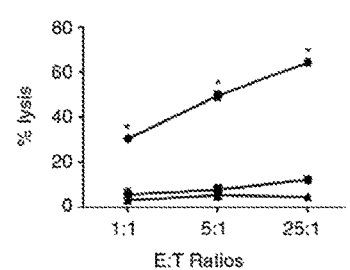
Figure 1F:
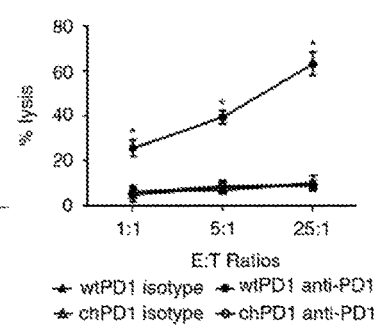

To determine if the murine lymphoma cell line RMA was a potential target of chPD1 T cells, the expression of PDL1 and PDL2 was measured. RMA cells expressed cell surface PDL1 and PDL2, as determined by flow cytometry (FIG. 1d). RT-PCR for PD1 ligands was also performed, and RMA cells expressed mRNA for PDL1 and PDL2. The chPD1 T cells lysed RMA cells significantly more than T cells expressing a wtPD1 receptor or non-transduced, effector T cells (FIG. 1e). This lysis was dependent on the PD1 receptor because incubating the T cells with blocking anti-PD1 antibodies before the assay abolished the killing of tumor cells by chPD1 T cells (FIG. 1f).

Figure 2A:
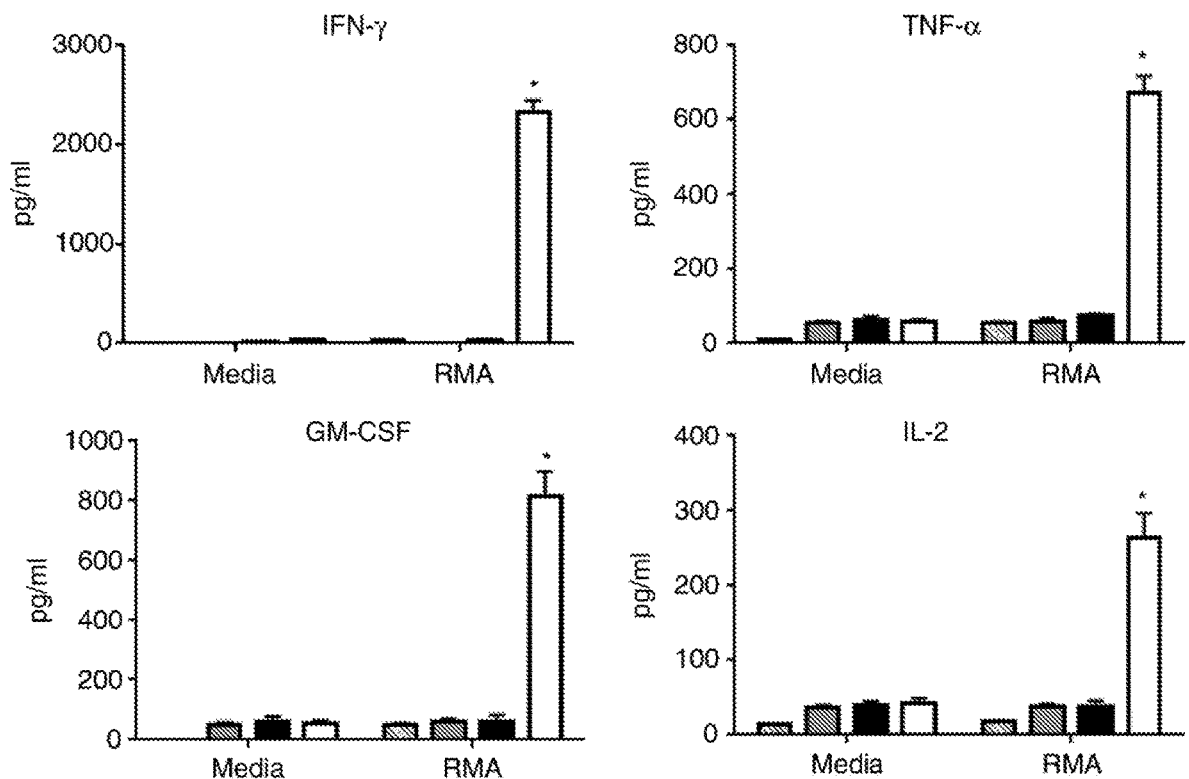
FIG. 2A-B. Culture of RMA cells with chimeric programmed death 1 (chPD1) T cells results in secretion of pro-inflammatory cytokines. Non-transduced, wild-type (wt) PD1-expressing (black), or chPD1-expressing (open) T cells were cultured with RMA cells or media. After 24 hr, secretion of (a) pro-inflammatory cytokines interferon-γ (IFN-γ), tumor necrosis factor-α (TNF-α), granulocyte-macrophage colony-stimulating factor (GM-CSF) and inter-leukin-2 (IL-2) and (b) anti-inflammatory cytokine IL-10 was measured in cell-free supernatants by ELISA. The chPD1 T cells produced higher levels of pro-inflammatory cytokines and decreased levels of anti-inflammatory cytokines compared with wtPD1 T cells when cultured with RMA cells (*P<0•001). Data are presented as mean+SD and are representative of at least three experiments.
Figure 2B:
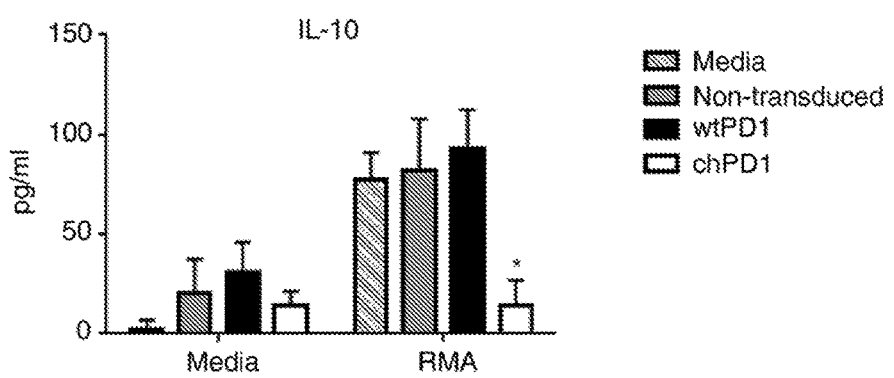

In addition to tumor cell lysis, T cells secrete pro-inflammatory cytokines to enhance antitumor immunity.[15, 30] Compared with non-transduced or wtPD1 T cells, chPD1 T cells secreted significant amounts of pro-inflammatory cytokines IFN-γ, TNF-α, GM-CSF and IL-2 but did not secrete anti-inflammatory cytokine IL-10 when cultured with RMA cells. (FIG. 2). Together, these data show that RMA cells expressed PD1 ligands and that expression of the chPD1 receptor induced pro-inflammatory cytokine secretion and lysis of the RMA murine lymphoma cell line.

Figure 3A:
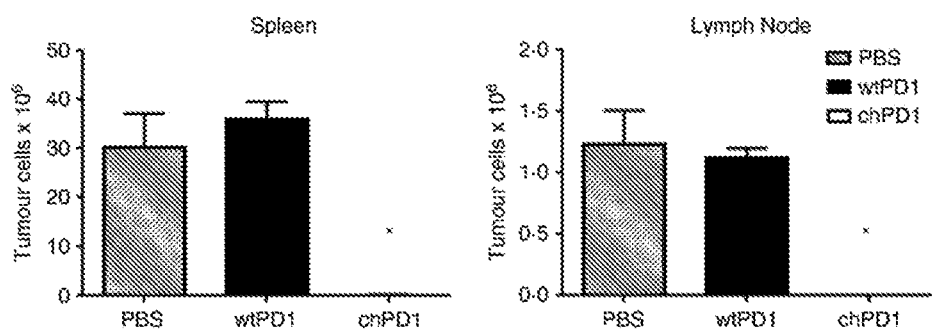
FIG. 3A-D. Treatment with chimeric programmed death 1 (chPD1) T cells leads to a reduction in tumor burden and an increase in survival of RMA-GFP-bearing mice. RMA-GFP cells ($2\times10^6$) were injected intravenously (i.v.) into B6 mice on day 0. Mice were treated i.v. with a single treatment of PBS or wild-type (wt) PD1 (black) or chPD1 (open) T cells ($5\times10^6$) after (a) 2 days, (b) 5 days or (c) two doses of wtPD1 or chPD1 T cells after 5 and 8 days. Mice were killed 13 days after RMA-GFP cell injection and tumor burden was determined by calculating the number of RMA-GFP cells in the spleen and lymph node (n=6). (d) Mice were treated i.v. with two doses of wtPD1- or chPD1 T cells after 5 and 12 days and survival of the mice was determined (n=7). The chPD1 T cells significantly reduced RMA tumor burden and increased survival compared with wtPD1 T cells or PBS (*P<0•01). Data are presented as mean+SD and are representative of two independent experiments.

Treatment with chPD1 T Cells Leads to a Reduction in Tumor Burden and an Increase in Survival of RMA-GFP-Bearing Mice When injected intravenously into mice, RMA tumor cells traffic to the spleen and lymph nodes; hence, this model recapitulates features of human lymphoma in syngeneic, immunocompetent mice.[31] Therefore, the potential of using chPD1 T cells in vivo as a therapy for lymphoma was investigated. Because ligands for PD1 may also be expressed on healthy tissues, the safety of chPD1 T cells was first tested. The chPD1 T cells did not lyse or secrete IFN-γ when cultured with splenocytes, liver cells or lung cells isolated from a naive mouse. In addition, after injection of chPD1 T cells, naive mice did not show any adverse symptoms or increased levels of serum IFN-γ, suggesting that chPD1 T cells did not target healthy tissues. Next, to test the anti-tumor efficacy of chPD1 T cells, lymphoma-bearing mice were treated with a single dose of chPD1 T cells 2 days after tumor cell injection and tumor burden was measured in the spleen and lymph nodes (FIG. 3a). Compared with mice treated with PBS or wtPD1 T cells, RMA tumor burden was significantly decreased in mice treated with chPD1 T cells. The tumor burden in mice treated with PBS or wtPD1 T cells was not significantly different, indicating that wtPD1 T cells did not decrease tumor burden.

Figure 3B:
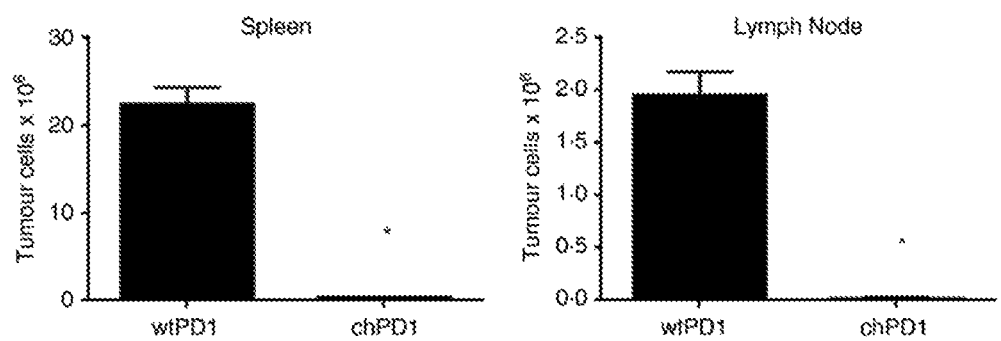
Figure 3C:
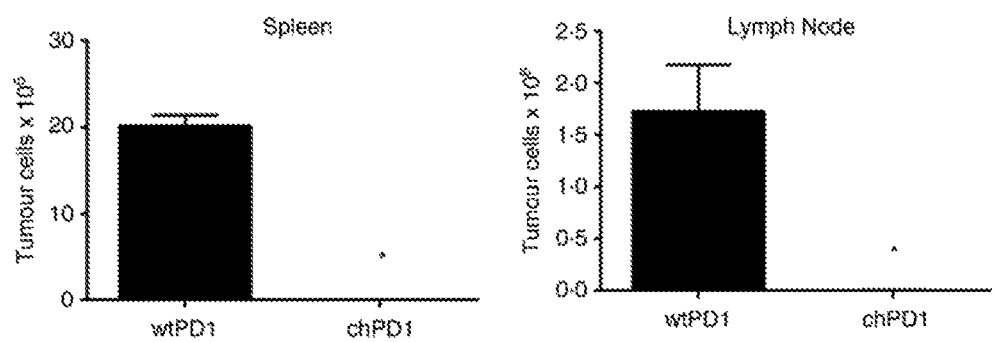
Figure 3D:
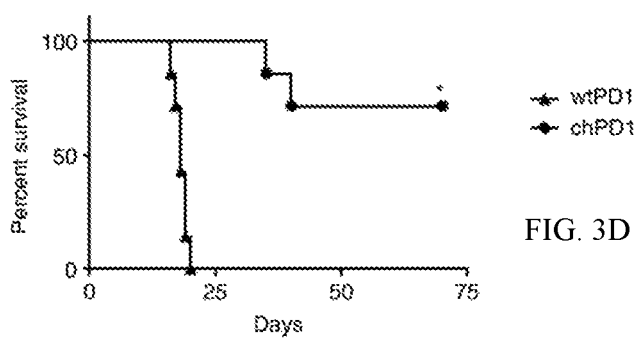
Figure 4A:
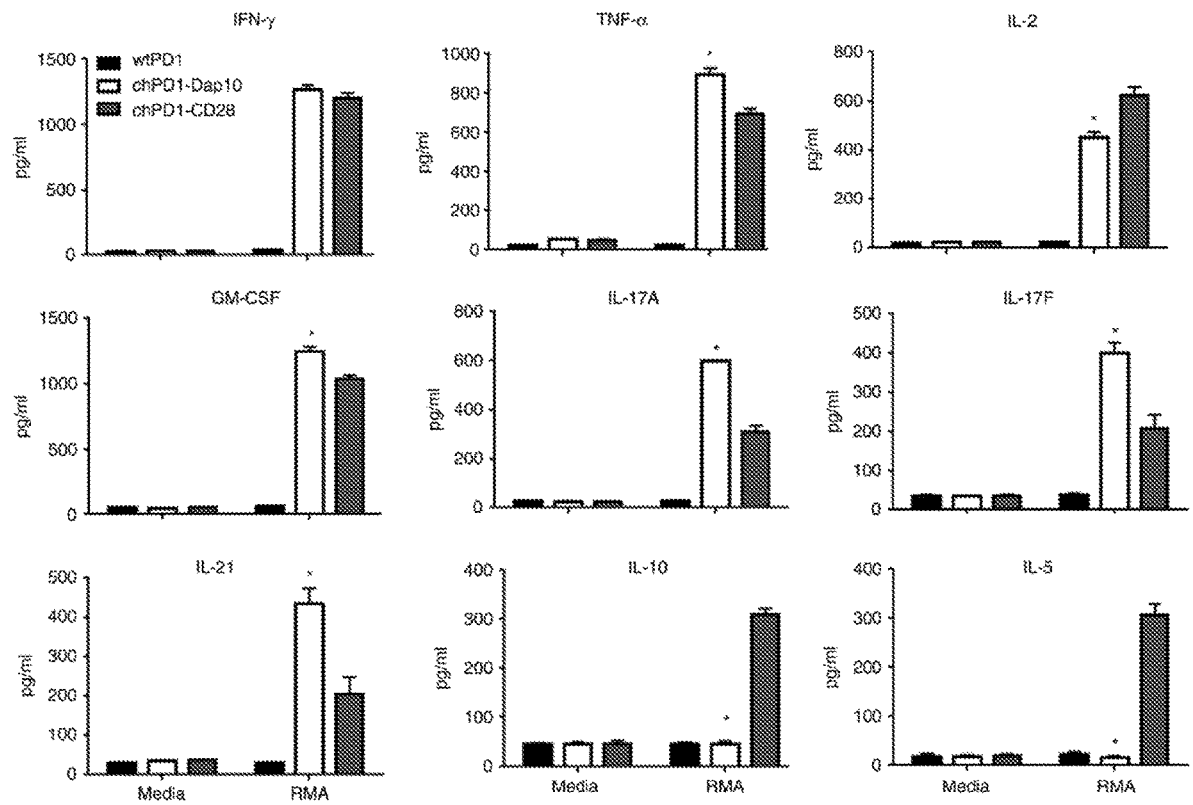
FIG. 4A-C. Chimeric programmed death 1 (chPD1)-Dap10 T cells secrete increased levels of pro-inflammatory cytokines and decreased levels of anti-inflammatory cytokines compared with chPD1-CD28 T cells. T cells expressing wild-type (wt) PD1-(black), chPD1-Dap10 (open), or chPD1-CD28 were cultured with RMA cells or media. After 24 hr, secretion of (a) cytokines and (b) chemokines was measured in cell-free supernatants by ELISA or LEGENDplex analysis. The chPD1-Dap10 T cells produced higher levels of pro-inflammatory cytokines and decreased levels of anti-inflammatory cytokines compared with wtPD1- or chPD1-CD28 T cells when cultured with RMA cells (*P<0•01). (c) wtPD1 (triangles), chPD1-Dap10 (circles), or chPD1-CD28 (diamonds) T cells were used as effector cells with RMA cells at the indicated effector tp target (E:T) ratios (1:1, 5:1, 25:1) and cell lysis was measured using a lactate dehydrogenase assay. Data are presented as mean+SD and are representative of at least three experiments.

To test the in vivo therapeutic efficacy of chPD1 T cells against a more established tumor burden, mice were treated with wtPD1 or chPD1 T cells 5 days after tumor cell injection. Treatment with chPD1 T cells significantly reduced these established tumors, although there was a low yet detectable level of tumor cells in the spleens and lymph nodes of the chPD1 T-cell-treated mice (FIG. 3b). As previous studies have shown that multiple treatments with CAR T cells enhance anti-tumor efficacy, tumor-bearing mice were injected with two treatments of wtPD1 or chPD1 T cells 5 and 8 days after tumor cell injection.[3, 30-32] Mice treated with two doses of chPD1 T cells had undetectable tumor levels of tumor cells (FIG. 3c). In addition, compared with mice treated with wtPD1 T cells that succumbed to tumors by day 20 after tumor cell injection, mice treated with two doses of chPD1 T cells had a significant increase in survival and there was long-term, tumor-free survival in 70% of lymphoma-bearing mice (FIG. 3d). These data show that chPD1 T-cell treatment of established lymphoma increased survival, and multiple doses of chPD1 T cells led to long-term survival in tumor-bearing mice.

chPD1-Dap10 T Cells Secrete Increased Levels of Pro-Inflammatory Cytokines and Decreased Levels of Anti-Inflammatory Cytokines Compared with chPD1-CD28 T Cells The inclusion of co-stimulatory domains in CARs enhances T-cell anti-tumor effector functions and each co-stimulatory receptor has a unique effect on T cells.[15, 16] Therefore to compare the inclusion of the Dap10 domain with another co-stimulatory receptor, a chPD1 receptor was made that contained the cytoplasmic domain of CD28 instead of the Dap10 cytoplasmic domain (FIG. 1a). One effector function that often differs between co-stimulatory receptors is their ability to induce cytokine secretion.[26-28] Therefore, the secretion of pro- and anti-inflammatory cytokines by chPD1-Dap10 and chPD1-CD28 T cells was compared. Although secretion of IFN-γ was similar, chPD1-Dap10 T cells secreted higher amounts of pro-inflammatory cytokines TNF-α, GM-CSF, IL-17 and IL-21. Comparatively, chPD1-CD28 T cells secreted more IL-2 and T helper type 2/anti-inflammatory cytokines IL-5 and IL-10 (FIG. 4a). The chPD1-Dap10 and chPD1-CD28 T cells also secreted similar amounts of inflammatory chemokines regulated on activation, normal T cell expressed and secreted (RANTES) macrophage inflammatory proteins 1α and 1β. Although the cytokine secretion profile of the two CARs was different, there was no significant difference in T-cell proliferation, survival or tumor cell lysis by chPD1-Dap10 and chPD1-CD28 T cells (FIG. 4c). Hence, there were some significant differences in the effector functions induced by these receptors, particularly with the induction of differential cytokine secretion.

Figure 5A:
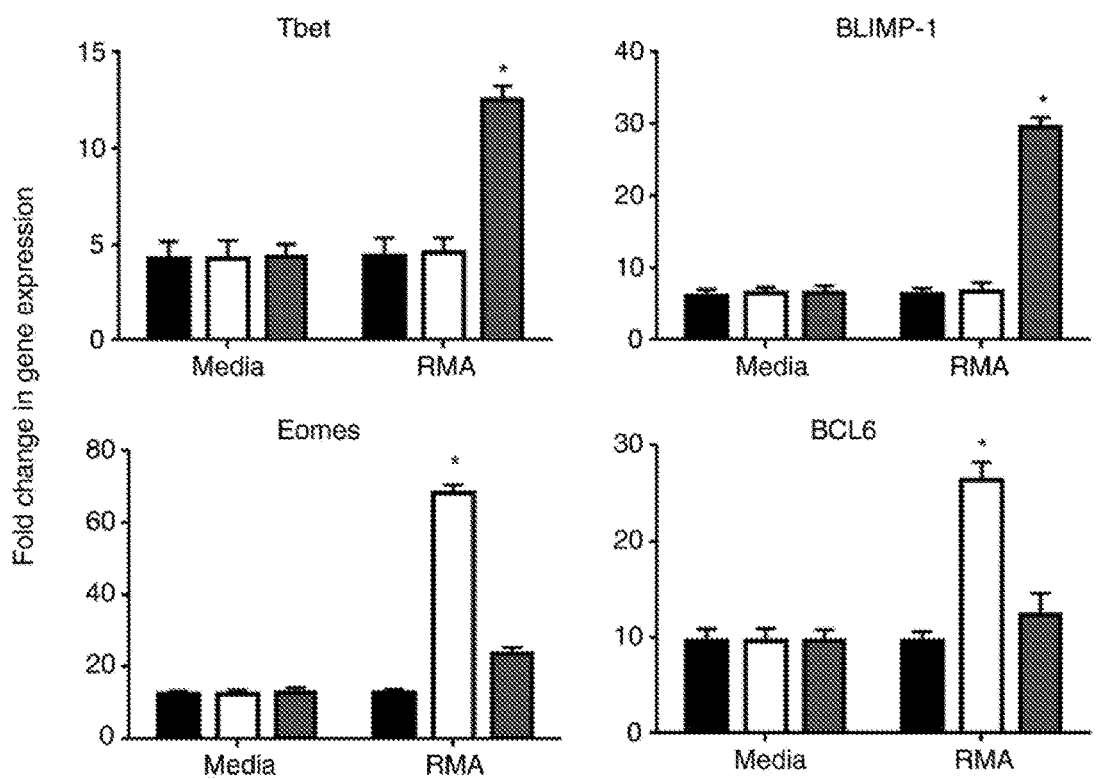
FIG. 5A-B. Inclusion of Dap10 co-stimulatory domain induces a central memory phenotype in chimeric programmed death 1 (chPD1) T cells. T cells expressing wild-type (wt) PD1-(black), chPD1-Dap10 (open), or chPD1-CD28 were cultured with RMA cells or media. After 24 hr, (a) expression of genes that control effector and central memory differentiation was measured by RT-PCR or (b) cell surface marker expression was measured by flow cytometry. Stimulation with RMA cells altered gene or cell surface marker expression compared with culturing in media (*P<0•01). Data are presented as mean+SD and are representative of at least two experiments.
Figure 5B:
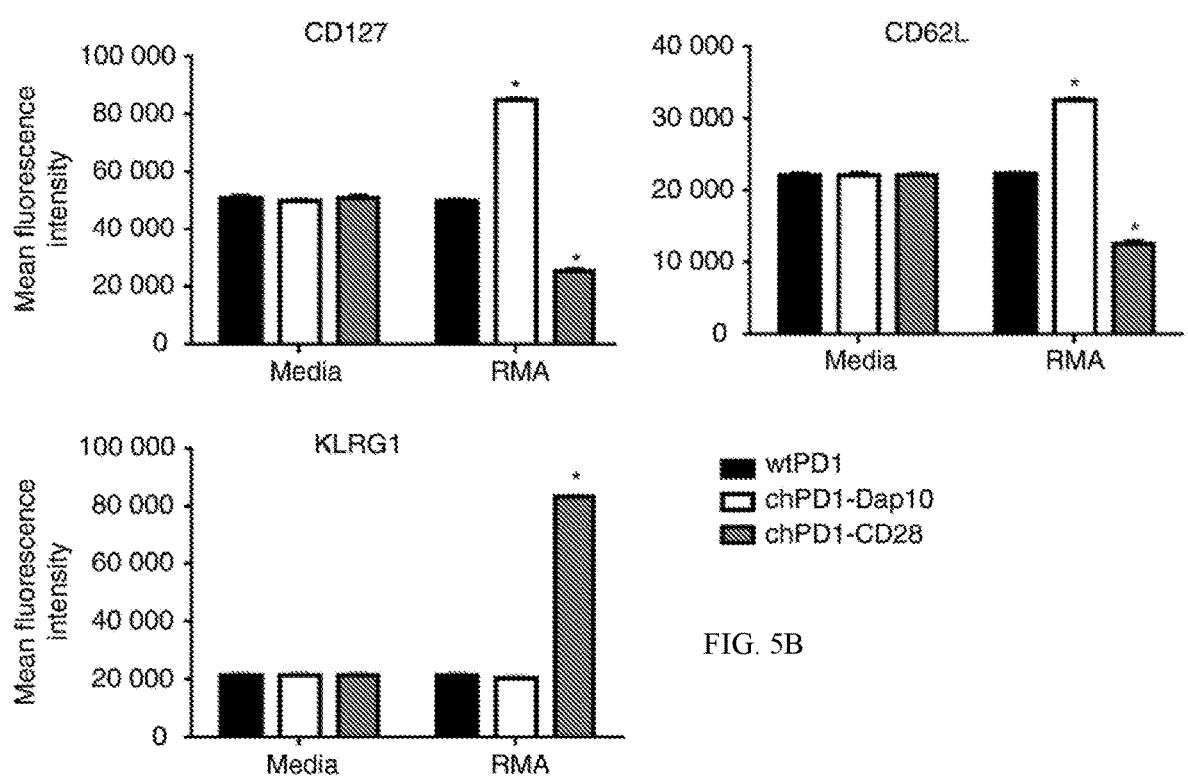

Inclusion of Dap10 Co-Stimulatory Domain Induces a Central Memory Phenotype in chPD1 T Cells Another characteristic that is important for CAR T-cell efficacy is the differentiation phenotype of the T cells. CD28-containing CARs often induce an effector memory or effector cell phenotype and do not live as long in vivo whereas CARs that induce a central memory phenotype usually persist longer in vivo and often have stronger anti-tumor efficacy.[3] Stimulation of natural killer group 2D (NKG2D)/Dap10 has recently been shown to induce a central memory phenotype in murine effector CD8 cells, so the differentiation phenotype of chPD1-Dap10 and chPD1-CD28 T cells was compared.[29] When cultured with RMA cells, chPD1-CD28 T cells increased the gene expression of transcription factors involved in effector cell differentiation, T-bet and BLIMP-1, whereas chPD1-Dap10 T cells increased the expression of transcription factors that support central memory differentiation, Eomes and BCL-6 (FIG. 5a). Additionally, chPD1-Dap10 T cells expressed cell surface markers associated with a central memory phenotype ($CD127^{hi}$, $CD62L^{hi}$, $KLRG1^{lo}$) and chPD1-CD28 T cells expressed effector memory phenotype markers ($CD127^{lo}$, $CD62L^{lo}$, $KLRG1^{hi}$) (FIG. 5b). These data indicate that the chPD1-Dap10 and chPD1-CD28 receptors induce different T-cell phenotypes, which could contribute to altered in vivo anti-tumor efficacy.

Figure 6A:
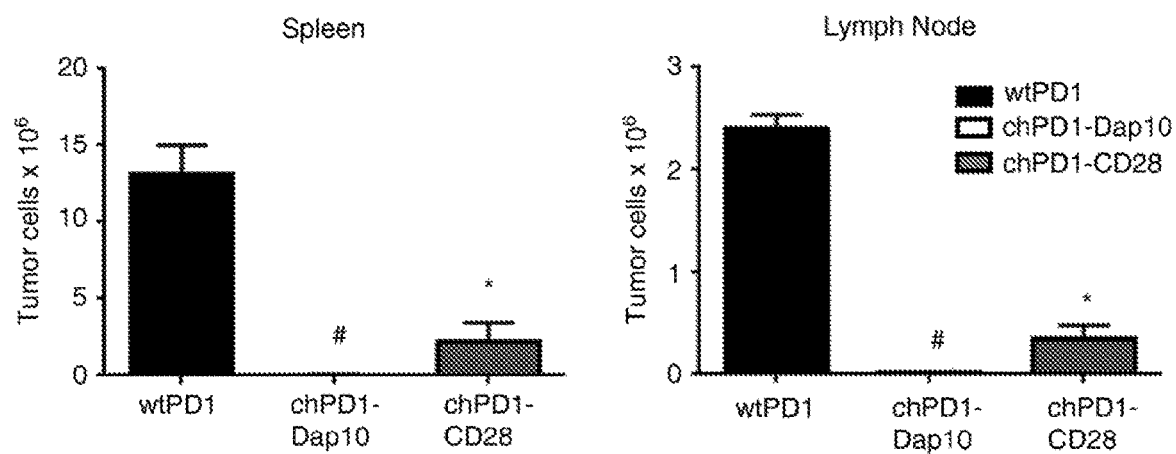
FIG. 6A-C. Treatment with chimeric programmed death 1 (chPD1)-Dap10 T cells leads to a greater reduction in tumor burden and increased survival of RMA-GFP-bearing mice compared with treatment with chPD1-CD28 T cells. RMA-GFP cells ($2\times10^6$) were injected intravenously (i.v.) into B6 mice on day 0. Mice were treated i.v. with two doses of wild-type (wt) PD1 (black), chPD1-Dap10 (open), or chPD1-CD28 T cells ($5\times10^6$) after 5 and 8 days. (a) Mice were killed 13 days after RMA-GFP cell injection and tumor burden was determined by calculating the number of RMA-GFP cells in the spleen and lymph node (n=6). (b) Survival of the mice was determined (n=6). The chPD1-CD28 T cells significantly reduced RMA tumor burden and increased survival compared with wtPD1 T cells (*P<0•01). chPD1-Dap10 T cells significantly reduced RMA tumor burden and increased survival better than chPD1-CD28 T cells (#P<0•01). (c) RMA-bearing mice were treated with $5\times10^6$ Ly5.1+ chPD1-Dap10 (open) or chPD1-CD28 T cells i.v. 5 days after tumor cell injection. Spleen and lymph node cells were isolated at various time-points after T-cell injection and the percentage of Ly5.1+CD3+ cells was calculated (n=4). chPD1-Dap10 T cells had increased persistence in vivo compared with chPD1-CD28 T cells (*P<0•01). Data are presented as mean+SD and are representative of two independent experiments.
Figure 6B:
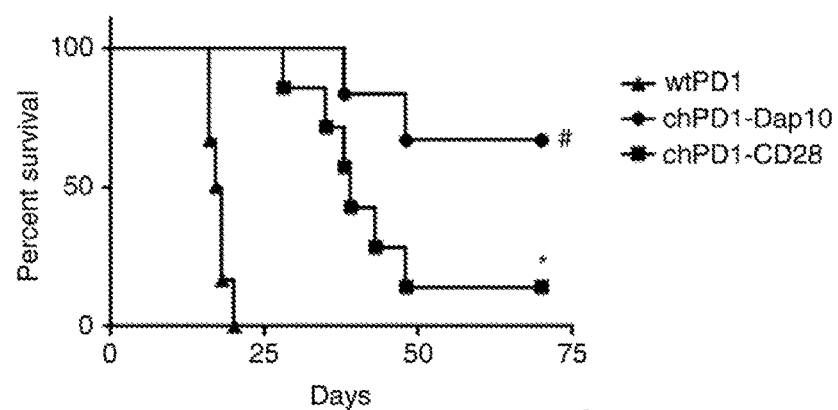
Figure 6C:
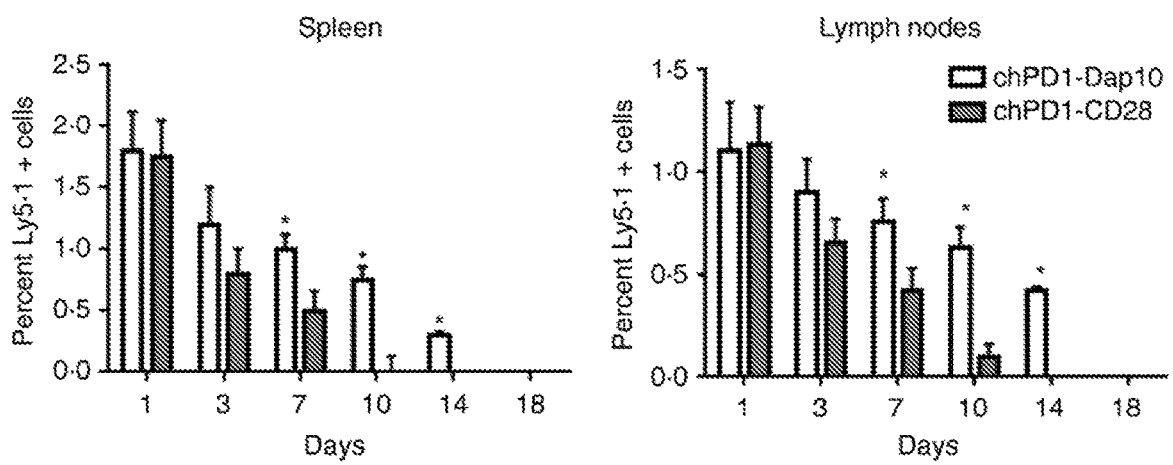

Treatment with chPD1-Dap10 T Cells Leads to a Greater Reduction in Tumor Burden and Increased Survival of RMA-GFP-Bearing Mice Compared with Treatment with chPD1-CD28 T Cells To compare the in vivo therapeutic efficacy of chPD1-Dap10 and chPD1-CD28 T cells, lymphoma-bearing mice were treated with two doses of wtPD1, chPD1-Dap10 or chPD1-CD28 T cells. Treatment with chPD1-Dap10 or chPD1-CD28 T cells significantly reduced tumor burden, but chPD1-Dap10 T cells reduced tumor burden significantly more than chPD1-CD28 T cells (FIG. 6a). In addition, treatment with two doses of chPD1-Dap10 T cells led to long-term, tumor-free survival in a higher percentage of mice (66% of mice) compared with mice treated with chPD1-CD28 T cells (14% of mice) (FIG. 6b). One potential factor that contributed to the enhanced anti-tumor efficacy of chPD1-Dap10 T cells was their increased in vivo persistence in the spleens and lymph nodes of lymphoma-bearing mice (FIG. 6c). Ly5.1+ chPD1-Dap10 T cells were still detectable by flow cytometry in the spleen and lymph nodes 14 days after T-cell injection, whereas the chPD1-CD28 T cells were not detected after day 10. Taken together, these data indicate that chPD1 T cells can reduce tumor burden and increase survival in this mouse model of lymphoma and that inclusion of a Dap10 co-stimulatory domain has enhanced in vivo therapeutic efficacy compared with a CD28-containing chPD1 receptor.

Discussion

The introduction of CARs has dramatically increased the potential efficacy of T-cell therapy for cancer.[1, 3, 33] However, the up-regulation of inhibitory receptor expression on T cells, including expression of the PD1 receptor, and expression of inhibitory ligands in the tumor microenvironment limit CAR T-cell responses and efficacy.[9, 34-36] This study demonstrates that expression of the novel chPD1 receptor enhances T-cell anti-tumor efficacy in a mouse model of lymphoma. Our results suggest that chPD1 receptor-transduced T cells target PDL expression on tumors and that interaction with PDL induces activation instead of inhibition of the T cells. The chPD1-expressing T cells secreted pro-inflammatory cytokines and lysed PDL-expressing tumor cells and also reduced tumor burden and increased tumor-free survival in lymphoma-bearing mice. In addition, the chPD1 receptor containing a Dap10 co-stimulatory domain was functionally superior compared with the chPD1 receptor containing a CD28 co-stimulatory domain.

Many new mechanisms to shield T cells from PD1 inhibition are being developed. In addition to PD1 blockade, expression of a PD1-CD28 switch receptor, which replaces the cytoplasmic domain of PD1 with the cytoplasmic domain of CD28, has been shown to prevent T-cell inhibition.[37-40] When co-expressed with a tumor-specific T-cell receptor or CAR, the PD1-CD28 switch receptor induces T-cell activation as shown by extracellular signal regulated kinase phosphorylation, cytokine secretion, proliferation, granzyme B expression and enhanced anti-tumor function.[37-40] primary goal of our study was to test the efficacy of T cells expressing a CAR that directly connects the PD1-extracellular domain to the intracellular domains of Dap10 or CD28 and CD3ζ, so providing both the activation and co-stimulatory signal all within the same receptor and eliminating the need for co-expressing two receptors in the T cells. Furthermore, many of the previous PD1 switch receptor studies tested the anti-tumor efficacy of human T cells in immunodeficient mouse models.[37, 38] However, CAR T cells often require the induction of host immune responses for full anti-tumor efficacy.[15, 30-32] In addition, testing human CAR T-cell efficacy in immunodeficient mice does not investigate the role of other immune cells, including myeloid-derived suppressor cells and regulatory T cells, in the anti-tumor immune response. Therefore, the creation of a murine chPD1 receptor allows the study of chPD1 T-cell efficacy in an immunocompetent host and represents the tumor microenvironment the T cells would be likely to encounter in patients.

The inclusion of a co-stimulatory domain in CARs increases antitumor efficacy and the majority of CAR T-cell clinical trials are using second-generation CARs consisting of CD3ζ and CD28 or 4-1BB co-stimulatory domains.[1, 3, 4, 15, 16, 33, 41] One difference that is observed between CAR T cells with CD28 or 4-1BB signalling domains is that inclusion of 4-1BB induces a central memory phenotype, and these T cells persist longer in vivo, and have stronger anti-tumor efficacy whereas T cells with a CD28-CAR induce an effector memory or effector cell phenotype and do not live as long in vivo.[3, 42] The induction of a central memory phenotype in T cells expressing a 4-1BB-containing CAR was partially caused by a distinct metabolic signature that included enhanced respiratory capacity, increased fatty acid oxidation and enhanced mitochondrial biogenesis, whereas CAR T cells with CD28 domains induced effector memory cells and had an enhanced glycolysis signature.[42] In the present study, the inclusion of the Dap10 co-stimulatory domain induced superior anti-tumor immunity in vivo. Without being bound by theory, this could potentially be caused by the induction of a central memory phenotype and enhanced in vivo survival of the chPD1-Dap10 T cells. Stimulation of NKG2D/Dap10 has recently been shown to induce a central memory phenotype in murine effector CD8 cells in part due to differential activation of mTOR.[29] Interestingly, mTOR activates specific metabolic pathways in T cells such as aerobic glycolysis and compared with CD28 co-stimulation, activation through NKG2D/Dap10 shows weaker activation of mTOR.[29, 43] Hence, the induction of mTOR activation, metabolism and cell differentiation are likely key characteristics in CAR T-cell success.

Figure 4B:
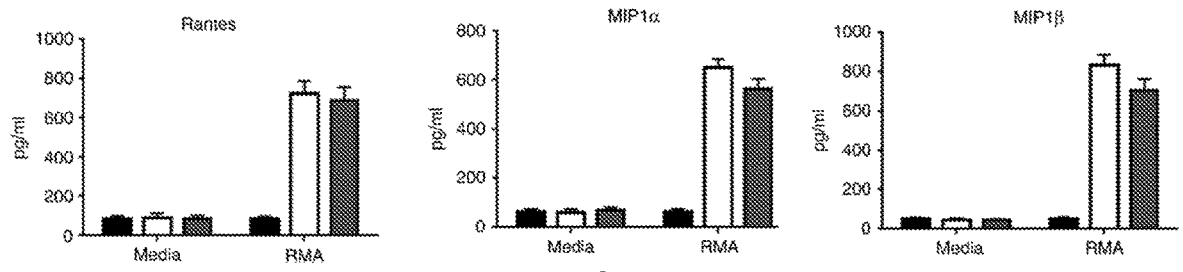
Figure 4C:
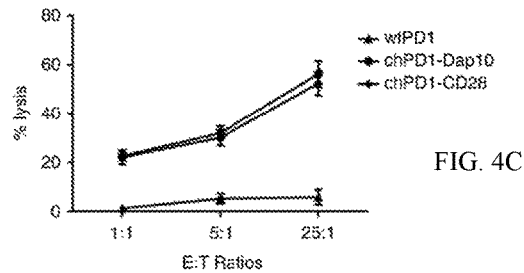

In the clinic, one of the adverse effects following infusion of CAR T cells is the onset of immune activation, known as cytokine release syndrome.[44, 45] This may include elevation of cytokines including IFN-γ, GM-CSF, IL-10 and IL-6 following CAR T-cell infusion and the dramatic increase in cytokines generally correlates with expansion and activation of adoptively transferred cells.[45] In this study, one difference observed between chPD1-Dap10 and chPD1-CD28 T cells was the differential expression of cytokines, with chPD1-Dap10 T cells secreting higher amounts of pro-inflammatory cytokines TNF-α, GM-CSF, IL-17 and IL-21 and chPD1-CD28 T cells secreting more IL-2 and T helper type 2/anti-inflammatory cytokines IL-5 and IL-10 (FIG. 4). Although the secretion of pro-inflammatory cytokines is beneficial for anti-tumor immunity and the concurrent secretion of anti-inflammatory cytokines can inhibit the immune response, the challenge may lie in selecting the appropriate CAR design to mitigate or prevent uncontrolled inflammation without hindering the antitumor efficacy of T cells. Tumor-bearing mice receiving chPD1 T cells did not show any adverse effects following treatment and survived long-term; however, the degree of cytokine release syndrome severity is probably dictated by disease burden at the time of infusion.[44-47] Although the high secretion of inflammatory cytokines from chPD1-Dap10 T cells probably contributes to their stronger anti-tumor efficacy, one can monitor cytokine release syndrome symptoms in mice with even higher tumor burdens to determine if the secretion of pro-inflammatory cytokines may induce damaging amounts of inflammation. In addition, chPD1-Dap10 T cells may be combined with agents that prevent cytokine release syndrome, such as IL-6R blockade.

In this study, inclusion of the Dap10 co-stimulatory domain in the chPD1 receptor did not induce secretion of IL-10 whereas inclusion of the CD28 domain did. CD28-induced secretion of IL-10 has been shown to alter T-cell anti-tumor responses through down-regulation of MHC molecules, CD28 ligands and intercellular adhesion molecule-1 on antigen-presenting cells.[48] As a consequence, host T-cell responses are inhibited and the secretion of pro-inflammatory cytokines is repressed. In addition, secretion of anti-inflammatory cytokines has been shown to not only inhibit CAR T-cell efficacy but also to induce chronic toxicity in some studies.[49] Therefore, without being bound by theory, the decrease in IL-10 secretion from chPD1-Dap10 T cells may contribute to their enhanced in vivo anti-tumor efficacy.

In summary, a new chPD1 receptor was developed that induces strong antitumor T-cell responses and induction of long-term, tumor-free survival in an immunocompetent mouse model of lymphoma. The strong induction of pro-inflammatory cytokines induced by inclusion of a Dap10 co-stimulatory receptor may be beneficial for anti-tumor therapy.

Example 2. Human T Cells Expressing a Chimeric-PD1-Dap10 Receptor as an Immunotherapy Adoptive transfer of tumor-reactive T cells is a promising anti-tumor therapy for many cancers. To enhance tumor recognition by T cells, chimeric antigen receptors (CAR) consisting of signaling domains fused to receptors that recognize tumor antigens can be created and expressed in T cells. As presented in Example 1, one receptor that is a target for a new chimeric antigen receptor is PD1 because the ligands for the PD1 receptor are expressed on many cancer types. In the present study, a human chimeric PD1 receptor (chPD1) consisting of the PD1 receptor extracellular domain and the activation domain of CD3 zeta was developed. The Dap10 costimulatory domain was also included in the chPD1 receptor as discussed in Example 1. The nucleic acid sequence of the CAR is presented in SEQ ID NO: 2 and the amino acid sequence is presented in SEQ ID NO: 3. To determine if this novel CAR could target a wide variety of tumors, the anti-tumor efficacy of chPD1 T cells against human lymphoma, melanoma, myeloma, pancreatic, breast, and ovarian cancer cell lines was measured. Of the eight cell lines tested, all expressed PD1 ligands on their cell surface, making them potential targets for chPD1 T cells. The chPD1 receptor was successfully expressed on the surface of human T cells and expression of chPD1 T cells induced significant tumor cell lysis of all tumor cell lines and secreted pro-inflammatory (IFNγ, TNFα, IL-2, GM-CSF, IL-17, and IL-21) cytokines. Therefore, adoptive transfer of chPD1-Dap10 T cells represents a novel therapeutic strategy to treat multiple types of cancer.

REFERENCES

1 Johnson L A, June C H. Driving gene-engineered T cell immunotherapy of cancer. *Cell Res* 2017; 27:38-58.
2 Chmielewski M, Hombach A A, Abken H. Antigen-specific T-cell activation independently of the MHC: chimeric antigen receptor-redirected T cells. *Front Immunol* 2013; 4:371.
3 Holzinger A, Barden M, Abken H. The growing world of CAR T cell trials: a systematic review. *Cancer Immunol Immunother* 2016; 65:1433-50.
4 Yong C S, Dardalhon V, Devaud C, Taylor N, Darcy P K, Kershaw M H. CAR T-cell therapy of solid tumors. *Immunol Cell Biol* 2017; 95:356-63.
5 Wherry E J. T cell exhaustion. *Nat Immunol* 2011; 12:492-9.
6 Speiser D E, Ho P C, Verdeil G. Regulatory circuits of T cell function in cancer. *Nat Rev Immunol* 2016; 16:599-611.
7 Chemnitz J M, Parry R V, Nichols K E, June C H, Riley J L. SHP-1 and SHP-2 associate with immunoreceptor tyrosine-based switch motif of programmed death 1 upon primary human T cell stimulation, but only receptor ligation prevents T cell activation. *J Immunol* 2004; 173:945-54.
8 Ahmadzadeh M, Johnson L A, Heemskerk B, Wunderlich J R, Dudley M E, White D E, Rosenberg S A. Tumor antigen-specific CD8 T cells infiltrating the tumor express high levels of PD-1 and are functionally impaired. *Blood* 2009; 114:1537-44.
9 Pardoll D M. The blockade of immune checkpoints in cancer immunotherapy. *Nat Rev Cancer* 2012; 12:252-64.
10 Kamphorst A O, Ahmed R. Manipulating the PD-1 pathway to improve immunity. *Curr Opin Immunol* 2013; 25:381-8.
11 Postow M A, Callahan M K, Wolchok J D. Immune checkpoint blockade in cancer therapy. *J Clin Oncol* 2015; 33:1974-82.
12 Bardhan K, Anagnostou T, Boussiotis V A. The PD1: PD-L1/2 pathway from discovery to clinical implementation. *Front Immunol* 2016; 7:550.
13 Xia Y, Jeffrey Medeiros L, Young K H. Signaling pathway and dysregulation of PD1 and its ligands in lymphoid malignancies. *Biochim Biophys Acta* 2016; 1865:58-71.
14 Ansell S M. Where do programmed death-1 inhibitors fit in the management of malignant lymphoma? *J Oncol Pract* 2016; 12:101-6.
15 Redeker A, Arens R. Improving adoptive T cell therapy: the particular role of T cell costimulation, cytokines, and post-transfer vaccination. *Front Immunol* 2016; 7:345.
16 Hornbach A A, Holzinger A, Abken H. The weal and woe of costimulation in the adoptive therapy of cancer with chimeric antigen receptor (CAR)-redirected T cells. *Curr Mol Med* 2013; 13:1079-88.
17 Savoldo B, Ramos C A, Liu E, Mims M P, Keating M J, Carrum G et al. CD28 costimulation improves expansion and persistence of chimeric antigen receptor-modified T cells in lymphoma patients. *J Clin Invest* 2011; 121:1822-6.
18 Kowolik C M, Topp M S, Gonzalez S, Pfeiffer T, Olivares S, Gonzalez N et al. CD28 costimulation provided through a CD19 specific chimeric antigen receptor enhances in vivo persistence and antitumor efficacy of adoptively transferred T cells. *Cancer Res* 2006; 66:10995-1004.
19 Sadelain M, Brentjens R, Riviere I. The basic principles of chimeric antigen receptor design. *Cancer Discov* 2013; 3:388-98.
20 Benitez A C, Dai Z, Mann H H, Reeves R S, Margineantu D H, Gooley T A et al. Expression, signaling proficiency, and stimulatory function of the NKG2D lymphocyte receptor in human cancer cells. *Proc Natl Acad Sci USA* 2011; 108:4081-6.
21 Kim E H, Sullivan J A, Plisch E H, Tejera M M, Jatzek A, Choi K Y et al. Signal integration by Akt regulates CD8 T cell effector and memory differentiation. *J Immunol* 2012; 188:4305-14.
22 Colombetti S, Basso V, Mueller D L, Mondino A. Prolonged TCR/CD28 engagement drives IL-2-independent T cell clonal expansion through signaling mediated by the mammalian target of rapamycin. *J Immunol* 2006; 176:2730-8.

23 Upshaw J L, Leibson P J. NKG2D-mediated activation of cytotoxic lymphocytes: unique signaling pathways and distinct functional outcomes. *Semin Immunol* 2006; 18:167-75.

24 Maasho K, Opoku-Anane J, Marusina A I, Coligan J E, Borrego F. NKG2D is a costimulatory receptor for human naive CD8+ T cells. *J Immunol* 2005; 174:4480-4.

25 Markiewicz M A, Carayannopoulos L N, Naidenko O V, Matsui K, Burack W R, Wise E L et al. Costimulation through NKG2D enhances murine CD8+ CTL function: similarities and differences between NKG2D and CD28 costimulation. *J Immunol* 2005; 175:2825-33.

26 Rajasekaran K, Xiong V, Fong L, Gorski J, Malarkannan S. Functional dichotomy between NKG2D and CD28-mediated co-stimulation in human CD8+ T cells. *PLoS ONE* 2010; 5:e12635.

27 Barber A, Sentman C L. NKG2D receptor regulates human effector T-cell cytokine production. *Blood* 2011; 117:6571-81.

28 Whitman E, Barber A. NKG2D receptor activation of NF-κB enhances inflammatory cytokine production in murine effector CD8+ T cells. *Mol Immunol* 2015; 63:268-78.

29 McQueen B, Trace K, Whitman E, Bedsworth T, Barber A. NKG2D and CD28 receptors differentially activate mTOR to alter murine effector CD8+ T cell differentiation. *Immunology* 2016; 147:305-20.

30 Barber A, Zhang T, Sentman C L. Immunotherapy with chimeric NKG2D receptors leads to long-term tumor-free survival and development of host antitumor immunity in murine ovarian cancer. *J Immunol* 2008; 180:72-8.

31 Zhang T, Barber A, Sentman C L. Chimeric NKG2D modified T cells inhibit systemic T-cell lymphoma growth in a manner involving multiple cytokines and cytotoxic pathways. *Cancer Res* 2007; 67:11029-36.

32 Barber A, Sentman C L. Chimeric NKG2D T cells require both T cell- and host-derived cytokine secretion and perforin expression to increase tumor antigen presentation and systemic immunity. *J Immunol* 2009; 183: 2365-72.

33 Lim W A, June C H. The principles of engineering immune cells to treat cancer. *Cell* 2017; 168:724-40.

34 Ito T, Ueno T, Clarkson M R, Yuan X, Jurewicz M M, Yagita H et al. Analysis of the role of negative T cell costimulatory pathways in CD4 and CD8 T cell-mediated alloimmune responses in vivo. *J Immunol* 2005; 174: 6648-56.

35 Blank C, Mackensen A. Contribution of the PD-L1/PD-1 pathway to T-cell exhaustion: an update on implications for chronic infections and tumor evasion. *Cancer Immunol Immunother* 2007; 56:739-45.

36 Morales-Kastresana A, Labiano S, Quetglas J I, Melero I. Better performance of CARs deprived of the PD-1 brake. *Clin Cancer Res* 2013; 19:5546-8.

37 Prosser M E, Brown C E, Shami A F, Forman S J, Jensen M C. Tumor PD-L1 co-stimulates primary human CD8+ cytotoxic T cells modified to express a PD1:CD28 chimeric receptor. *Mol Immunol* 2012; 51:263-72.

38 Ankri C, Shamalov K, Horovitz-Fried M, Mauer S, Cohen C J. Human T cells engineered to express a programmed death 1/28 costimulatory retargeting molecule display enhanced antitumor activity. *J Immunol* 2013; 191:4121-9.

39 Liu X, Ranganathan R, Jiang S, Fang C, Sun J, Kim S et al. A chimeric switch-receptor targeting PD1 augments the efficacy of second-generation CAR T cells in advanced solid tumors. *Cancer Res* 2016; 76:1578-90.

40 Kobold S, Grassmann S, Chaloupka M, Lampert C, Wenk S, Kraus F et al. Impact of a new fusion receptor on PD-1-mediated immunosuppression in adoptive T cell therapy. *J Natl Cancer Inst* 2015; 107:djv146.

41 Hombach A A, Abken H. Of chimeric antigen receptors and antibodies: OX40 and 41BB costimulation sharpen up T cell-based immunotherapy of cancer. *Immunotherapy* 2013; 5:677-81.

42 Kawalekar O U, O'Connor R S, Fraietta J A, Guo L, McGettigan S E, Posey A D et al. Distinct signaling of coreceptors regulates specific metabolism pathways and impacts memory development in CAR T cells. *Immunity* 2016; 44:380-90.

43 Yang K, Chi H. mTOR and metabolic pathways in T cell quiescence and functional activation. *Semin Immunol* 2012; 24:421-8.

44 Lee D W, Gardner R, Porter D L, Louis C U, Ahmed N, Jensen M et al. Current concepts in the diagnosis and management of cytokine release syndrome. *Blood* 2014; 124:188-95.

45 Bonifant C L, Jackson H J, Brentjens R, Curran K J. Toxicity and management in CAR T-cell therapy. *Mol Ther Oncolytics* 2016; 3:16011.

46 Davila M L, Riviere I, Wang X, Bartido S, Park J, Curran K et al. Efficacy and toxicity management of 19-28z CAR T cell therapy in B cell acute lymphoblastic leukemia. *Sci Transl Med* 2014; 6:224ra25.

47 Lee D W, Kochenderfer J N, Stetler-Stevenson M, Cui Y K, Delbrook C, Feldman S A et al. T cells expressing CD19 chimeric antigen receptors for acute lymphoblastic leukaemia in children and young adults: a phase 1 dose-escalation trial. *Lancet* 2015; 385:517-28.

48 Hombach A A, Heiders J, Foppe M, Chmielewski M, Abkem H. Ox40 costimulation by a chimeric antigen receptor abrogates CD28 and IL-2 induced IL-10 secretion by redirected CD4 T cells. *Oncoimmunology* 2012; 1:458-66.

49 Cheadle E J, Sheard V, Rothwell D G, Bridgeman J S, Ashton G, Hanson V et al. Differential role of Th1 and Th2 cytokines in autotoxicity driven by CD19-specific second-generation chimeric antigen receptor T cells in a mouse model. *J Immunol* 2014; 192:3654-65.

While the invention has been described in its preferred embodiments, those of skill in the art will recognize the invention can be practiced with variations within the spirit and scope of the appended claims.

The invention claimed is:

1. A chimeric antigen receptor (CAR) polypeptide comprising the CAR polypeptide sequence of SEQ ID NO: 3.

2. A vector comprising a nucleic acid encoding the CAR polypeptide according to claim 1.

3. A T lymphocyte genetically modified to express a CAR according to claim 1.

4. A composition for adoptive cell transfer comprising T lymphocytes according to claim 3 and a pharmaceutically acceptable carrier.

5. The composition of claim 4, further comprising one or more chemotherapeutic or radiotherapeutic agents.

6. A method of treating cancer in a subject in need thereof, wherein cells of said cancer express at least one of PDL1 and PDL2, comprising: administering to the subject a therapeutically effective amount of a composition for adoptive cell transfer comprising T lymphocytes comprising a polynucleotide encoding the CAR polypeptide of claim 1.

7. The method of claim 6, wherein the polynucleotide encoding the CAR polypeptide comprises a sequence at least 90% identical to SEQ ID NO: 2.

8. The method of claim 6, wherein said cancer is selected from the group consisting of lymphoma, melanoma, myeloma, pancreatic cancer, breast cancer, and ovarian cancer.

9. The method of claim 6, further comprising a step of administering one or more of a chemotherapeutic or radiotherapeutic agent.

* * * * *

SEQUENCE LISTING

<160> NUMBER OF SEQ ID NOS: 9

<210> SEQ ID NO 1
<211> LENGTH: 288
<212> TYPE: PRT
<213> ORGANISM: Homo sapiens

<400> SEQUENCE: 1

```
Met Gln Ile Pro Gln Ala Pro Trp Pro Val Val Trp Ala Val Leu Gln
1               5                   10                  15
Leu Gly Trp Arg Pro Gly Trp Phe Leu Asp Ser Pro Asp Arg Pro Trp
            20                  25                  30
Asn Pro Pro Thr Phe Ser Pro Ala Leu Leu Val Val Thr Glu Gly Asp
        35                  40                  45
Asn Ala Thr Phe Thr Cys Ser Phe Ser Asn Thr Ser Glu Ser Phe Val
    50                  55                  60
Leu Asn Trp Tyr Arg Met Ser Pro Ser Asn Gln Thr Asp Lys Leu Ala
65                  70                  75                  80
Ala Phe Pro Glu Asp Arg Ser Gln Pro Gly Gln Asp Cys Arg Phe Arg
                85                  90                  95
Val Thr Gln Leu Pro Asn Gly Arg Asp Phe His Met Ser Val Val Arg
            100                 105                 110
Ala Arg Arg Asn Asp Ser Gly Thr Tyr Leu Cys Gly Ala Ile Ser Leu
        115                 120                 125
Ala Pro Lys Ala Gln Ile Lys Glu Ser Leu Arg Ala Glu Leu Arg Val
    130                 135                 140
Thr Glu Arg Arg Ala Glu Val Pro Thr Ala His Pro Ser Pro Ser Pro
145                 150                 155                 160
Arg Pro Ala Gly Gln Phe Gln Thr Leu Val Val Gly Val Val Gly Gly
                165                 170                 175
Leu Leu Gly Ser Leu Val Leu Leu Val Trp Val Leu Ala Val Ile Cys
            180                 185                 190
Ser Arg Ala Ala Arg Gly Thr Ile Gly Ala Arg Arg Thr Gly Gln Pro
        195                 200                 205
Leu Lys Glu Asp Pro Ser Ala Val Pro Val Phe Ser Val Asp Tyr Gly
    210                 215                 220
Glu Leu Asp Phe Gln Trp Arg Glu Lys Thr Pro Glu Pro Pro Val Pro
225                 230                 235                 240
Cys Val Pro Glu Gln Thr Glu Tyr Ala Thr Ile Val Phe Pro Ser Gly
                245                 250                 255
Met Gly Thr Ser Ser Pro Ala Arg Arg Gly Ser Ala Asp Gly Pro Arg
            260                 265                 270
Ser Ala Gln Pro Leu Arg Pro Glu Asp Gly His Cys Ser Trp Pro Leu
        275                 280                 285
```

<210> SEQ ID NO 2
<211> LENGTH: 1079
<212> TYPE: DNA
<213> ORGANISM: Artificial Sequence
<220> FEATURE:
<223> OTHER INFORMATION: Synthetic chimeric antigen receptor

<400> SEQUENCE: 2

```
agtttccctt ccgctcacct ccgcctgagc agtggagaag gcggcactct ggtggggctg      60
ctccaggcat gcagatccca caggcgccct ggccagtcgt ctgggcggtg ctacaactgg     120
gctggcggcc aggatggttc ttagactccc cagacaggcc ctggaacccc ccacccttct     180
ccccagccct gctcgtggtg accgaagggg acaacgccac cttcacctgc agcttctcca     240
acacatcgga gagcttcgtg ctaaactggt accgcatgag cccagcaac cagacggaca     300 agctggccgc cttccccgag gaccgcagcc agcccggcca ggactgccgc ttccgtgtca     360
```

```
cacaactgcc caacgggcgt gacttccaca tgagcgtggt cagggcccgg cgcaatgaca    420
gcggcaccta cctctgtggg gccatctccc tggcccccaa ggcgcagatc aaagagagcc    480
tgcgggcaga gctcagggtg acagagagaa gggcagaagt gcccacagcc caccccagcc    540
cctcacccag gccagccggc cagttccaaa ccctggtgat ctacatctgg gcgcccttgg    600
ccgggacttg tggggtcctt ctcctgtcac tggttatcac cctgtgcgca cgcccacgcc    660
gcagccccgc caagaagat ggcaaagtct acatcaacat gccaggcagg ggcggtgtca    720
ttctcactgc cttgttcctg agagtgaagt tcagcaggag cgcagacgcc cccgcgtacc    780
agcagggcca gaaccagctc tataacgagc tcaatctagg acgaagagag gagtacgatg    840
ttttggacaa gagacgtggc cgggaccctg agatggggg aaagccgaga aggaagaacc    900
ctcaggaagg cctgtacaat gaactgcaga agataagat ggcggaggcc tacagtgaga    960
ttgggatgaa aggcgagcgc cggaggggca agggcacga tggcctttac cagggtctca    1020
gtacagccac caaggacacc tacgacgccc ttcacatgca ggccctgccc cctcgctaa    1079
```

<210> SEQ ID NO 3
<211> LENGTH: 337
<212> TYPE: PRT
<213> ORGANISM: Artificial Sequence
<220> FEATURE:
<223> OTHER INFORMATION: Synthetic chimeric antigen receptor

<400> SEQUENCE: 3

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Ile Tyr Ile Trp Ala Pro
                165                 170                 175

Leu Ala Gly Thr Cys Gly Val Leu Leu Leu Ser Leu Val Ile Thr Leu
            180                 185                 190

Cys Ala Arg Pro Arg Arg Ser Pro Ala Gln Glu Asp Gly Lys Val Tyr
        195                 200                 205

Ile Asn Met Pro Gly Arg Gly Gly Val Ile Leu Thr Ala Leu Phe Leu
    210                 215                 220

Arg Val Lys Phe Ser Arg Ser Ala Asp Ala Pro Ala Tyr Gln Gln Gly
225                 230                 235                 240
```

```
Gln Asn Gln Leu Tyr Asn Glu Leu Asn Leu Gly Arg Arg Glu Glu Tyr
            245                 250                 255

Asp Val Leu Asp Lys Arg Arg Gly Arg Asp Pro Glu Met Gly Gly Lys
        260                 265                 270

Pro Gln Arg Arg Lys Asn Pro Gln Glu Gly Leu Tyr Asn Glu Leu Gln
    275                 280                 285

Lys Asp Lys Met Ala Glu Ala Tyr Ser Glu Ile Gly Met Lys Gly Glu
290                 295                 300

Arg Arg Arg Gly Lys Gly His Asp Gly Leu Tyr Gln Gly Leu Ser Thr
305                 310                 315                 320

Ala Thr Lys Asp Thr Tyr Asp Ala Leu His Met Gln Ala Leu Pro Pro
            325                 330                 335

Arg

<210> SEQ ID NO 4
<211> LENGTH: 24
<212> TYPE: DNA
<213> ORGANISM: Artificial Sequence
<220> FEATURE:
<223> OTHER INFORMATION: Synthetic primer

<400> SEQUENCE: 4
gtgtgatggt gggaatgggt caga                                          24

<210> SEQ ID NO 5
<211> LENGTH: 24
<212> TYPE: DNA
<213> ORGANISM: Artificial Sequence
<220> FEATURE:
<223> OTHER INFORMATION: Synthetic primer

<400> SEQUENCE: 5
tacgaccaga ggcatacagg gaca                                          24

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
gctccaaagg acttgtacgt g                                             21

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
tgatctgaag ggcagcattt c                                             21

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
ctgccgatac tgaacctgag c                                             21
```

```
<210> SEQ ID NO 9
<211> LENGTH: 18
<212> TYPE: DNA
<213> ORGANISM: Artificial Sequence
<220> FEATURE:
<223> OTHER INFORMATION: Synthetic primer

<400> SEQUENCE: 9
gcggtcaaaa tcgcactc                                                      18
```